(12) United States Patent
Anderskewitz et al.

(10) Patent No.: US 6,780,863 B1
(45) Date of Patent: Aug. 24, 2004

(54) BIS-BASIC COMPOUNDS WITH TRYPTASE-INHIBITORY ACTIVITY

(75) Inventors: Ralf Anderskewitz, Bingen (DE); Christine Braun, Giubiasco (SE); Rainer Hamm, Ingelheim (DE); Bernd Disse, Mainz (DE); Hans Michael Jennewein, Wiesbaden (DE); Georg Speck, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 197 days.

(21) Appl. No.: 09/699,747

(22) Filed: Oct. 30, 2000

Related U.S. Application Data
(60) Provisional application No. 60/167,774, filed on Nov. 29, 1999.

(30) Foreign Application Priority Data
Nov. 18, 1999 (DE) .......................................... 199 55 476

(51) Int. Cl.[7] ...................... A61K 31/497; A61K 31/44; C07D 401/00; C07D 211/08
(52) U.S. Cl. .................. 514/252.11; 514/334; 544/360; 546/191
(58) Field of Search ........................ 544/360; 546/191; 514/252.11, 334

(56) References Cited
FOREIGN PATENT DOCUMENTS
WO  WO 99/24395 A  5/1999

OTHER PUBLICATIONS
Ca 113:142000, "Long–lived radical ion pair state of zinc–prphyrin–viologen–quinone triad", Batova et al., 1990, 14(4), 269–71.*
Ca 130:60591, "1,2–Benzisothiazol–3–one 1,1–Dioxide Inhibitors of Human Mast Cell Tryptase", Combrink et al., Journal of Medicinal Chemistry (1998), 41 (24), 4854–4860.*
Ca 2001:202153, "Synthesis and SAR of a 4–carboxy–2–azetidinone series of mechanism–based tryptase inhibitors", Sutton et al.*
Ca 2003:184117, "Inhibitors of serine proteases as potential therapeutic agents: The road from Thrombin to Tryptase to cathepsin G", Maryanoff et al.*

* cited by examiner

Primary Examiner—Joseph K. McKane
Assistant Examiner—Binta Robinson

(74) Attorney, Agent, or Firm—Robert P. Raymond; Timothy X. Witkowski; Anthony P. Bottino

(57) ABSTRACT
Compounds of which the following are exemplary:

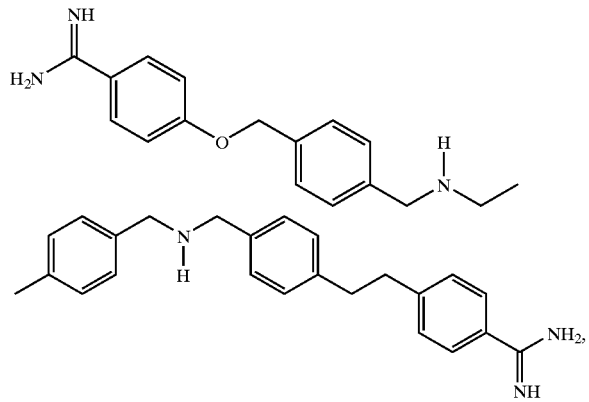

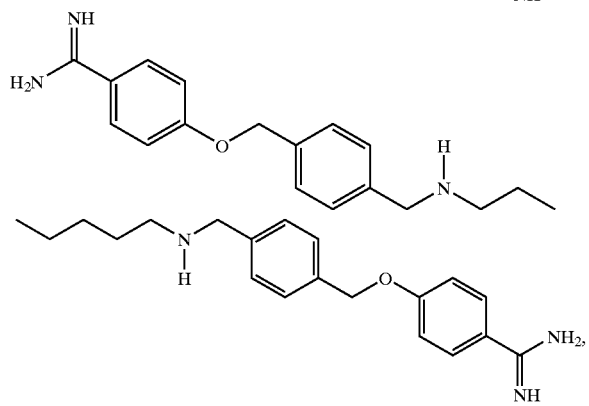

and

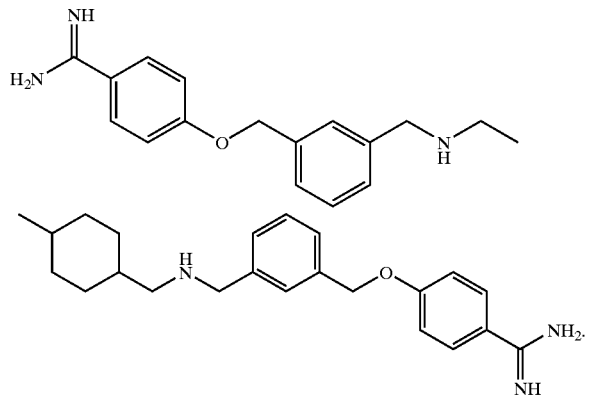

These have tryptase-inhibiting activity and are useful for the treatment of inflammatory and allergic disease conditions.

26 Claims, No Drawings

BIS-BASIC COMPOUNDS WITH TRYPTASE-INHIBITORY ACTIVITY

RELATED APPLICATIONS

Benefit of U.S. Provisional Application Serial No. 60/167,774, filed on Nov. 29, 1999 is hereby claimed.

FIELD OF THE INVENTION

The present invention relates to bis-basic compounds having tryptase-inhibiting activity, processes for preparing such compounds, their therapeutic use in the treatment of disease, and pharmaceutical compositions comprising such compounds.

SUMMARY OF THE INVENTION

Tryptase inhibitors may be used in the production of pharmaceutical compositions which are used to prevent and/or treat inflammatory and/or allergic conditions.

The object of the present invention is therefore to provide new compounds that have a tryptase-inhibiting activity and may be used to prevent and treat conditions in which tryptase inhibitors may have a therapeutic value.

DETAILED DESCRIPTION OF THE INVENTION

The compounds according to the invention are bis-basic compounds of general formula (I)

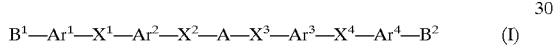

$$B^1-Ar^1-X^1-Ar^2-X^2-A-X^3-Ar^3-X^4-Ar^4-B^2 \qquad (I)$$

wherein
- $B^1$ and $B^2$ which may be identical or different denote $-C(=NR^1)-NR^{1'}H$, $-CH_2NH_2$, $-CH_2CH_2NH_2$ or $-NH-C(=NH)-NH_2$;
- $R^1$ and $R^{1'}$ which may be identical or different denote hydrogen, OH, $-COR^2$ or $-COOR^2$;
- $R^2$ denotes hydrogen, $C_1-C_{18}$-alkyl, aryl or aryl-$C_1-C_6$-alkyl;
- $Ar^1$, $Ar^2$, $Ar^3$, $Ar^4$ and aryl which may be identical or different denote $C_6-C_{10}$-aryl, which may optionally be mono- to tetrasubstituted by one or more groups selected from among $C_3-C_{10}$-cycloalkyl, F, Cl, Br, I, OH, $OR^3$, $SR^3$, $NR^3R^4$, $COOR^3$, $C_1-C_6$-alkyl, $C_2-C_6$-alkenyl and $C_2-C_6$-alkynyl, whilst in the substituents $C_1-C_6$-alkyl and $C_2-C_6$-alkenyl one or more hydrogen atoms may optionally be replaced by F or $OR^3$, or
- a 5–10-membered mono- or bicyclic heteroaryl ring, wherein up to three carbon atoms may be replaced by one or more heteroatoms selected from among oxygen, nitrogen and sulphur and which may optionally be mono- to tetrasubstituted by one or more groups selected from among $C_1-C_{10}$-cycloalkyl, F, Cl, Br, I, OH, $OR^3$, $SR^3$, $NR^3R^4$, $COOR^3$, $C_1-C_6$-alkyl, $C_2-C_6$-alkenyl and $C_2-C_6$-alkynyl, whilst in the substituents $C_1-C_6$-alkyl and $C_2-C_6$-alkenyl one or more hydrogen atoms may optionally be replaced by F or $OR^3$;
- $R^3$ and $R^4$ which may be identical or different denote hydrogen or a group selected from among $C_1-C_6$-alkyl and $C_3-C_6$-cycloalkyl wherein one or more hydrogen atoms may optionally be replaced by F;
- $X^1$, $X^2$, $X^3$ and $X^4$ which may be identical or different denote a bridge selected from among $-(CH_2)_n-$, $-(CH_2)_nO-$, $-(CH_2)_nS-$, $-(CH_2)_nNR^3-$ and $-(CH_2)_nN^+R^3R^4-$ where n=1 or 2;
- A denotes a group selected from among $C_2-C_{16}$-alkylene and $C_2-C_{16}$-alkenylene, wherein optionally one or more hydrogen atoms may be replaced by one or more groups selected from among F, $R^3$, $OR^3$ and $COOR^3$, or A denotes $C_2-C_{16}$-alkynylene, or
- A denotes $-(CH_2)_l-D-(CH_2)_m-$, whilst in the alkylene groups $-(CH_2)_l-$ and $-(CH_2)_m-$ one or two hydrogen atoms may optionally be replaced by $C_1-C_6$-alkyl and wherein
   - D denotes aryl or $C_3-C_{10}$-cycloalkyl wherein one or more hydrogen atoms may optionally be replaced by one or more groups selected from among F, $R^3$ and $OR^3$ and l and m, which may be identical or different, denote 0, 1, 2, 3 or 4,
   - or
   - D denotes $-O-$, $-S-$ or $-NR^3-$ and l and m, which may be identical or different, denote 2, 3 or 4;
   - or
- A denotes $-G^1-(CH_2)_r-G^2-$, if $X^2$ or $X^3$ denote $-(CH_2)_n-$, A may also denote $-E^1-(CH_2)_r-G^1-$ or $-E^1-(CH_2)_r-E^2-$,
   - wherein
   - r denotes the number 0, 1, 2, 3, 4, 5 or 6,
   - $G^1$ and $G^2$ which may be identical or different denote a single bond or $C_3-C_{10}$-cycloalkyl, but if r=0 or r=1 $G^1$ and $G^2$ cannot simultaneously represent a single bond;
   - $E^1$ and $E^2$ which may be identical or different denote $C_3-C_{10}$-aza-cycloalkyl which contains one or two nitrogen atoms, wherein at least one N-atom is bound to $X^2$ or $X^3=(CH_2)_n$, optionally in the form of their racemates, enantiomers, diastereomers, tautomers and mixtures thereof, and optionally the pharmacologically harmless acid addition salts thereof.

Preferred compounds of general formula (I) are those wherein
- $B^1$ and $B^2$ which may be identical or different denote $-C(=NR^1)-NR^{1'}H$, $-CH_2NH_2$, $-CH_2CH_2NH_2$ or $-NH-C(=NH)-NH_2$;
- $R^1$ and $R^{1'}$ which may be identical or different denote hydrogen, OH, $-COR^2$ or $-COOR^2$;
- $R^2$ denotes hydrogen, $C_1-C_{14}$-alkyl, aryl or aryl-$C_1-C_6$-alkyl;
- $Ar^1$, $Ar^2$, $Ar^3$, $Ar^4$ and aryl which may be identical or different, denote $C_6-C_{10}$-aryl which may optionally be mono- to tetrasubstituted by one or more groups selected from among $C_3-C_8$-cycloalkyl, F, Cl, Br, I, OH, $OR^3$, $NR^3R^4$, $COOR_3$, $C_1-C_6$-alkyl, $C_2-C_6$-alkenyl and $C_2-C_6$-alkynyl, whilst in the substituents $C_1-C_6$-alkyl and $C_2-C_6$-alkenyl one or more hydrogen atoms may optionally be replaced by F, or
- a 5–10-membered mono- or bicyclic heteroaryl ring, wherein up to three carbon atoms may be replaced by one or more heteroatoms selected from among oxygen, nitrogen and sulphur and which may optionally be mono- to tetrasubstituted by one or more groups selected from among F, $OR^3$, $COOR^3$ or $C_1-C_6$-alkyl, wherein in the substituent $C_1-C_6$-alkyl one or more hydrogen atoms may optionally be replaced by F;
- $R^3$ and $R^4$ which may be identical or different denote hydrogen or a group selected from among $C_1-C_6$-alkyl and $C_3-C_6$-cycloalkyl wherein one or more hydrogen atoms may optionally be replaced by F;
- $X^1$, $X^2$, $X^3$ and $X^4$ which may be identical or different denote a bridge selected from among $-(CH_2)_n-$, —$(CH_2)_nO$—, —$(CH_2)_n$—S—, —$(CH_2)_nNR^3$— and —$(CH_2)_nN^+R^3R^4$— where n=1 or 2;

A denotes a group selected from among $C_2$–$C_{14}$-alkylene and $C_2$–$C_{10}$-alkenylene, wherein optionally one or more hydrogen atoms may be replaced by one or more groups selected from among F, $R^3$, $OR^3$ and $COOR^3$, or A denotes $C_2$–$C_{10}$-alkynylene, or A denotes —$(CH_2)_l$—D—$(CH_2)_m$—, whilst in the alkylene groups —$(CH_2)_l$— and —$(CH_2)_m$— one or two hydrogen atoms may optionally be replaced by $C_1$–$C_6$-alkyl and wherein D denotes aryl or $C_3$–$C_8$-cycloalkyl wherein one or more hydrogen atoms may optionally be replaced by one or more groups selected from among F, $R^3$ and $OR^3$ and l and m, which may be identical or different, denote 0, 1, 2, 3 or 4, or D denotes —O—, —S— or —$NR^3$— and l and m, which may be identical or different, denote 2, 3 or 4;

or

A denotes —$G^1$—$(CH_2)_r$—$G^2$—, if $X^2$ or $X^3$ represents —$(CH_2)_n$—, A also denotes —$E^1$—$(CH_2)_r$—$G^1$— or —$E^1$—$(CH_2)_r$—$E^2$—, wherein r denotes the number 0, 1, 2, 3, 4, 5 or 6, $G^1$ and $G^2$ which may be identical or different denote a single bond or $C_3$–$C_8$-cycloalkyl, but if r=0 or r=1 $G^1$ and $G^2$ cannot simultaneously represent a single bond;

$E^1$ and $E^2$ which may be identical or different denote $C_3$–$C_8$-aza-cycloalkyl which contains one or two nitrogen atoms, wherein at least one N-atom is bound to $X^2$ or $X^3$=$(CH_2)_n$, optionally in the form of their racemates, enantiomers, diastereomers, tautomers and mixtures thereof, and optionally the pharmacologically harmless acid addition salts thereof.

Particularly preferred are compounds of general formula (I), wherein $B^1$ and $B^2$ which may be identical or different denote —C(=$NR^1$)—$NR^{1'}H$, —$CH_2NH_2$, —$CH_2CH_2NH_2$ or —NH—C(=NH)—$NH_2$;

$R^1$ and $R^{1'}$ which may be identical or different denote hydrogen, OH, —$COR^2$ or —$COOR^2$;

$R^2$ denotes hydrogen, $C_1$–$C_{10}$-alkyl or aryl-$C_1$–$C_4$-alkyl;

$Ar^1$, $Ar^2$, $Ar^3$, $Ar^4$ and aryl which may be identical or different, denote phenyl or naphthyl which may optionally be mono-, di— or trisubstituted by one or more groups selected from among F, $OR^3$, $NR^3R^4$, $COOR_3$ or $C_1$–$C_6$-alkyl, wherein in the substituent $C_1$–$C_6$-alkyl one or more hydrogen atoms may optionally be replaced by F or $OR^3$;

$R^3$ and $R^4$ which may be identical or different denote hydrogen or a group selected from among cyclopropyl, cyclopentyl, cyclohexyl and $C_1$–$C_4$-alkyl wherein one or more hydrogen atoms may optionally be replaced by F;

$X^1$, $X^2$, $X^3$ and $X^4$ which may be identical or different denote a bridge selected from among —$(CH_2)_n$—, —$(CH_2)_nO$—, —$(CH_2)_n$—S—, —$(CH_2)_nNR^3$— and —$(CH_2)_nN^+R^3R^4$— where n=1 or 2, preferably where n=1;

A denotes $C_2$–$C_{12}$-alkylene wherein optionally one or more hydrogen atoms may be replaced by one or more groups selected from among F, $OR^3$ and $COOR^3$, or A denotes —$(CH_2)_l$—D—$(CH_2)_m$—, whilst in the alkylene groups —$(CH_2)_l$— and —$(CH_2)_m$— one or two hydrogen atoms may optionally be replaced by a $C_1$–$C_4$ group and wherein D denotes a group selected from among phenyl, cyclopentyl and cyclohexyl wherein one or more hydrogen atoms may optionally be replaced by one or more groups selected from among F, $R^3$ and $OR^3$ and l and m, which may be identical or different, denote 0, 1, 2, 3 or 4, or D denotes —O— or —$NR^3$— and l and m, which may be identical or different, denote 2, 3 or 4;

or

A denotes —$G^1$—$(CH_2)_r$—$G^2$—, if $X^2$ or $X^3$ represents —$(CH_2)_n$—, A also denotes —$E^1$—$(CH_2)_r$—$G^1$— or —$E^1$—$(CH_2)_r$—$E^2$—, wherein r denotes the number 0, 1, 2, 3 or 4, $G^1$ and $G^2$ which may be identical or different denote a single bond, cyclopentyl, cyclohexyl or cycloheptyl, if r=0 or r=1 $G^1$ and $G^2$ cannot simultaneously represent a single bond;

$E^1$ and $E^2$ which may be identical or different denote a group selected from among pyrrolidine, imidazolidine, piperidine and piperazine, wherein at least one N-atom is bound to $X^2$ or $X^3$=$(CH_2)_n$, optionally in the form of their racemates, enantiomers, diastereomers, tautomers and mixtures thereof, and optionally the pharmacologically harmless acid addition salts thereof. Of particular importance according to the invention are compounds of general formula (I)

wherein $B^1$ and $B^2$ which may be identical or different denote —C(=$NR^1$)—$NR^{1'}H$, —$CH_2NH_2$, —$CH_2CH_2NH_2$ or —NH—C(=NH)—$NH_2$;

$R^1$ and $R^{1'}$ which may be identical or different denote hydrogen, OH, —$COR^2$ or —$COOR^2$, preferably hydrogen or OH, $R^2$ denotes hydrogen, $C_1$–$C_6$-alkyl or benzyl;

$Ar^1$, $Ar^2$, $Ar^3$ and $Ar^4$ which may be identical or different, denote phenyl which may optionally be mono-, di— or trisubstituted by one or more groups selected from among F, $OR^3$, $NR^3R^4$, $COOR_3$ or $C_1$–$C_4$-alkyl, wherein in the substituent $C_1$–$C_4$-alkyl one or more hydrogen atoms may optionally be replaced by F;

$R^3$ and $R^4$ which may be identical or different denote hydrogen or a group selected from among cyclopropyl, cyclopentyl, cyclohexyl and $C_1$–$C_4$-alkyl, wherein one or more hydrogen atoms may optionally be replaced by F;

$X^1$, $X^2$, $X^3$ and $X^4$ which may be identical or different denote a bridge selected from among —$(CH_2)_n$—, —$(CH_2)_nO$—, —$(CH_2)_n$—S—, —$(CH_2)_nNR^3$— and —$(CH_2)_nN^+R^3R^4$— where n=1 or 2, preferably where n=1; or A denotes $C_2$–$C_{12}$-alkylene wherein one or more hydrogen atoms may optionally be replaced by one or more groups selected from among F, $OR^3$ and $COOR^3$, or A denotes —$(CH_2)_l$—D—$(CH_2)_m$—, whilst in the alkylene groups —$(CH_2)_l$— and —$(CH_2)_m$— one or two hydrogen atoms may optionally be replaced by a methyl group and wherein D denotes a group selected from among phenyl and cyclohexyl wherein optionally one or more hydrogen atoms may be replaced by one or more groups selected from among F, $R^3$ and $OR^3$ and l and m, which may be identical or different, denote 0, 1, 2 or 3, or
  D denotes —O— and l and m, which may be identical or different, denote 2 or 3;
or
A denotes —G$^1$—(CH$_2$)$_r$—G$^2$—,
  if X$^2$ or X$^3$ represents —(CH$_2$)$_n$— A also denotes —E$^1$—(CH$_2$)$_r$—G$^1$— or —E$^1$—(CH$_2$)$_r$—E$^2$—,
  wherein
  r denotes the number 0, 1, 2 or 3,
  G$^1$ and G$^2$ which may be identical or different denote a single bond, cyclopentyl or cyclohexyl, but if r=0 or r=1 G$^1$ and G$^2$ cannot simultaneously represent a single bond;
  E$^1$ and E$^2$ which may be identical or different denote piperidine or piperazine, wherein at least one N-atom is bound to X$^2$ or X$^3$=(CH$_2$)$_n$,
optionally in the form of their racemates, enantiomers, diastereomers, tautomers and mixtures thereof, and optionally the pharmacologically harmless acid addition salts thereof.

Also of significance according to the invention are compounds of general formula (I),
wherein
  B$^1$ and B$^2$ which may be identical or different denote —C(=NR$^1$)—NH$_2$, —CH$_2$NH$_2$ or —CH$_2$CH$_2$NH$_2$;
  R$^1$ denotes hydrogen, OH, —COR$^2$ or —COOR$^2$, preferably hydrogen or OH,
  R$^2$ denotes hydrogen, methyl, ethyl, propyl, butyl, pentyl, hexyl or benzyl;
  Ar$^1$, Ar$^2$, Ar$^3$ and Ar$^4$, which may be identical or different, denote phenyl;
  X$^1$, X$^2$, X$^3$ and X$^4$ which may be identical or different denote a bridge selected from among —(CH$_2$)$_n$—, —(CH$_2$)$_n$O—, —(CH$_2$)$_n$NH—, —(CH$_2$)$_n$NMe—, —(CH$_2$)$_n$NEt—, —(CH$_2$)$_n$Nprop—, —(CH$_2$)$_n$Ncyclopropy—, —(CH$_2$)$_n$NBu— and —(CH$_2$)$_n$N$^+$(Me)$_2$ where n=1;
  A denotes C$_2$-C$_{12}$-alkylene which may optionally be substituted by a group selected from among OH, COOH and COOMe, or
  —(CH$_2$)$_l$—D—(CH$_2$)$_m$—, whilst in the alkylene groups —(CH$_2$)$_l$— and —(CH$_2$)$_m$— one or two hydrogen atoms may optionally be replaced by methyl and wherein
  D denotes phenyl or cyclohexyl which may optionally be substituted by methyl and l and m, which may be identical or different, denote 0, 1, 2 or 3,
  or
  D denotes —O— and l and m, which may be identical or different, represent 2 or 3;
or
A denotes —G$^1$—(CH$_2$)$_r$—G$^2$—,
  if X$^2$ or X$^3$ denotes —(CH$_2$)$_n$— A may also denote —E$^1$—(CH$_2$)$_r$—G$^1$— or —E$^1$—(CH$_2$)$_r$—E$^2$—,
  wherein
  r denotes the number 0, 1, 2 or 3,
  G$^1$ and G$^2$ which may be identical or different denote a single bond or cyclohexyl, but if r=0 or r=1 G$^1$ and G$^2$ cannot simultaneously represent a single bond;
  E$^1$ and E$^2$ which may be identical or different denote piperidine or piperazine, wherein at least one N-atom is bound to X$^2$ or X$^3$=(CH$_2$)$_n$,
optionally in the form of their racemates, enantiomers, diastereomers, tautomers and mixtures thereof, and optionally the pharmacologically harmless acid addition salts thereof.

Also preferred are compounds of general formula (IA)

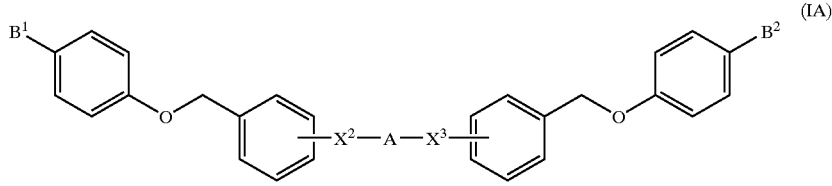

(IA)

wherein B1, B2, A, X$^2$ and X$^3$ have the meanings given hereinbefore and hereinafter, optionally in the form of their racemates, enantiomers, diastereomers, tautomers and mixtures thereof, and optionally the pharmacologically harmless acid addition salts thereof.

Of particular importance are the compounds of general formula (I) or (IA) according to the invention wherein the grouping B$^1$—Ar$^1$—X$^1$—Ar$^2$—X$^2$— denotes a group selected from among

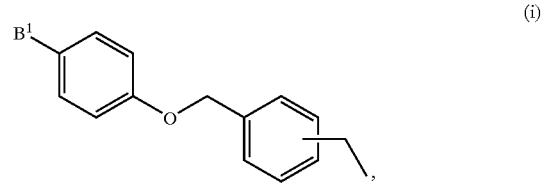

(i)

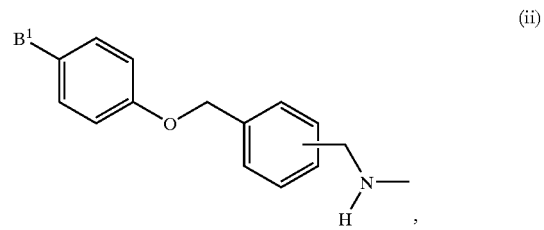

(ii)

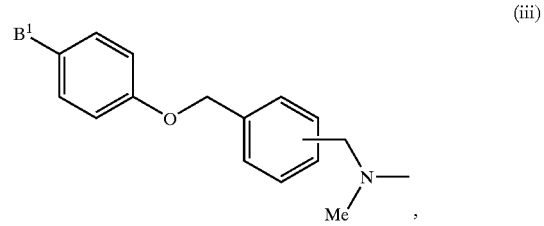

(iii)

(iv)
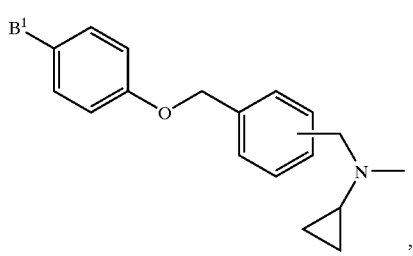

(v)
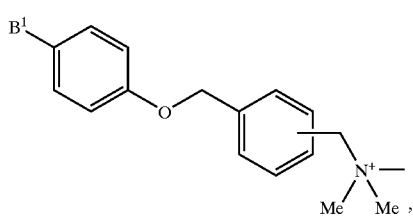

(vi)
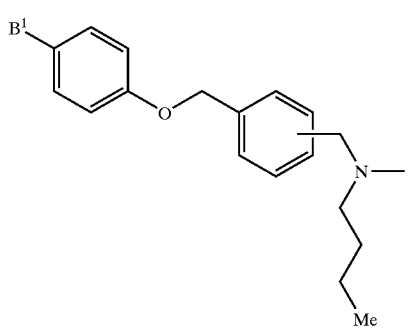

(vii)
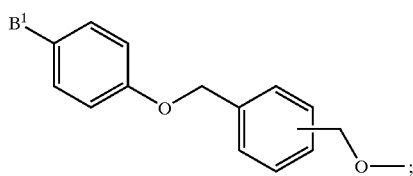

the grouping —X³—Ar³—X⁴—Ar⁴—B² denotes a group selected from among (i')
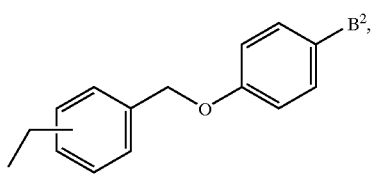

(ii')
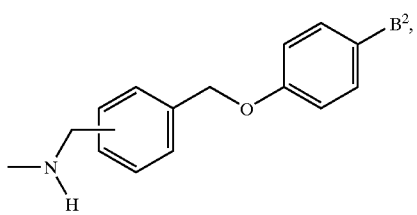

(iii')
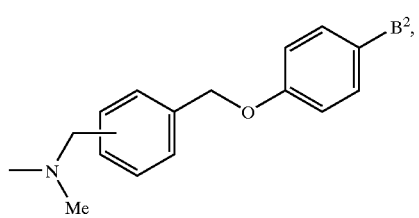

(iv')
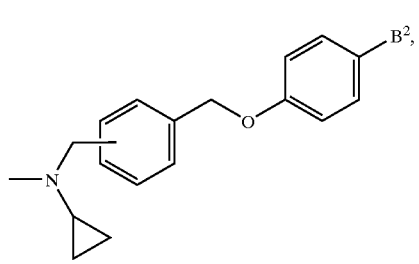

(v')
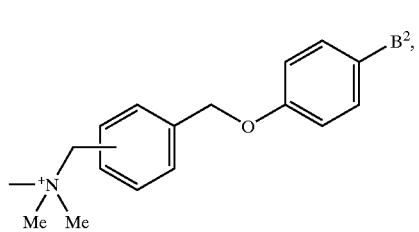

(vi')
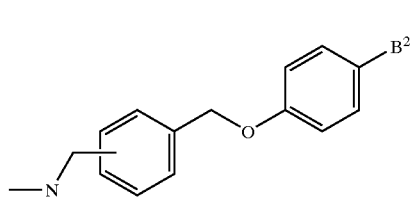

(vii')
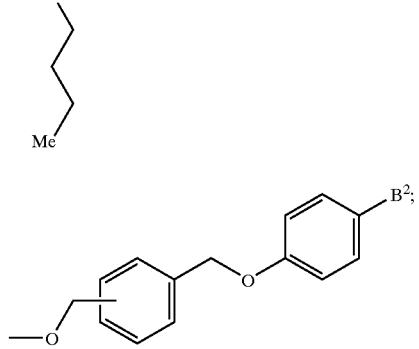

$B^1$ and $B^2$ which may be identical or different denote —C(=NR¹)—NR¹'H, —CH₂NH₂, —CH₂CH₂NH₂ or —NH—C(=NH)—NH₂;

$R^1$ and $R^{1'}$ which may be identical or different denote hydrogen or OH, preferably hydrogen;

A denotes a bridging group which is selected from among
(viii) $C_4$-$C_{10}$-alkylene which may optionally be substituted by COOH, (ix)

-continued

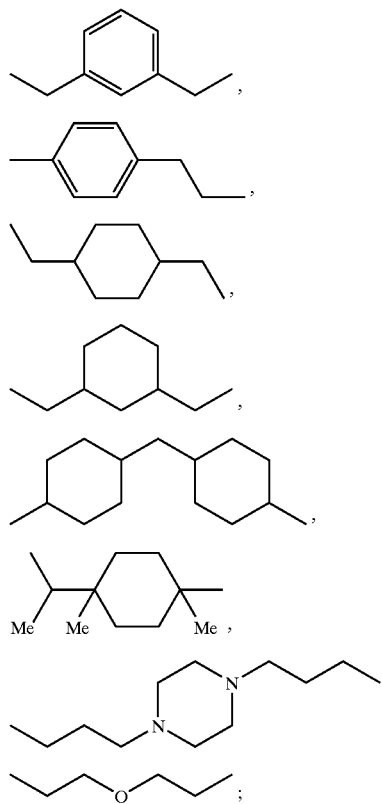

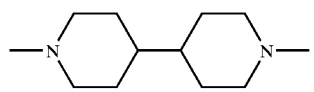

or
A may also denote

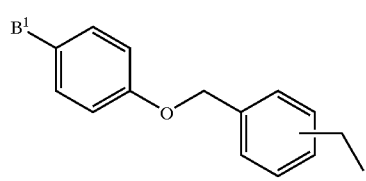

if the grouping $B^1$—$Ar^1$—$X^1$—$Ar^2$—$X^2$— represents the group

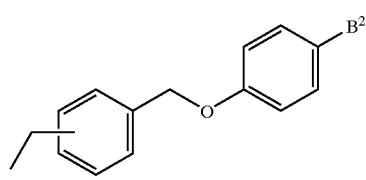

and the grouping —$X^3$—$Ar^3$—$X^4$—$Ar^4$—$B^2$ represents the group

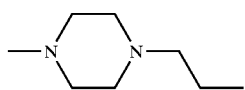

or
A may also denote

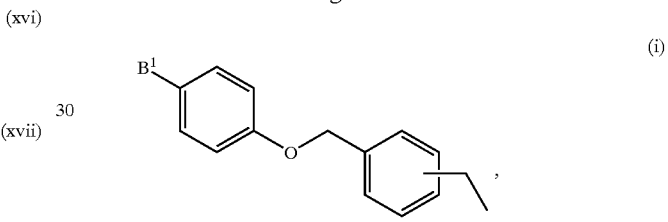

if the grouping of the two groups $B^1$—$Ar^1$—$X^1$—$Ar^2$—$X^2$— and —$X^3$—$Ar^3$—$X^4$—$Ar^4$—$B^2$ represents the group (i) or (i') which is bound directly to the piperazine-nitrogen of the group A, optionally in the form of their racemates, enantiomers, diastereomers, tautomers and mixtures thereof, and optionally the pharmacologically harmless acid addition salts thereof.

Also of special importance are the compounds of general formula (I) according to the invention wherein the grouping $B^1$—$Ar^1$—$X^1$—$Ar^2$—$X^2$— denotes a group selected from among

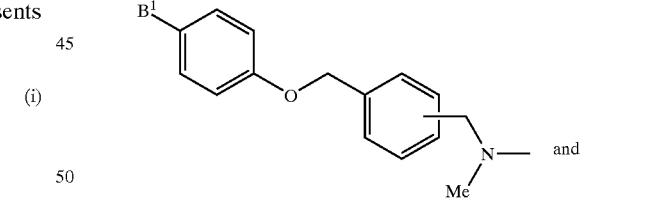

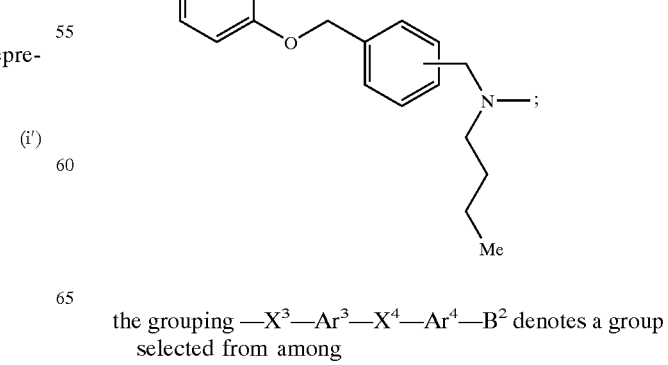

the grouping —$X^3$—$Ar^3$—$X^4$—$Ar^4$—$B^2$ denotes a group selected from among

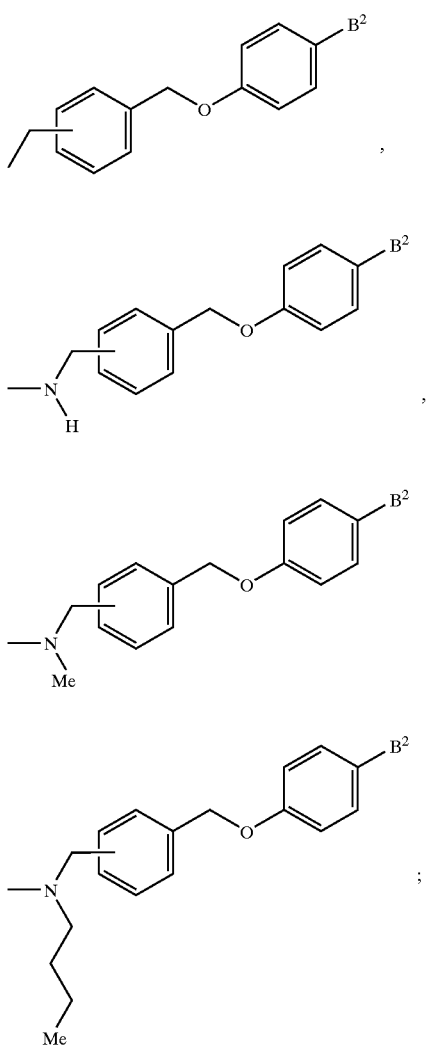

wherein
B¹ and B² which may be identical or different denote —C(=NR¹)—NR¹'H or —CH₂NH₂,
R¹ and R¹' which may be identical or different denote hydrogen or OH, preferably hydrogen;

A denotes a bridging group which is selected from among
(viii) $C_4$–$C_{10}$-alkylene,

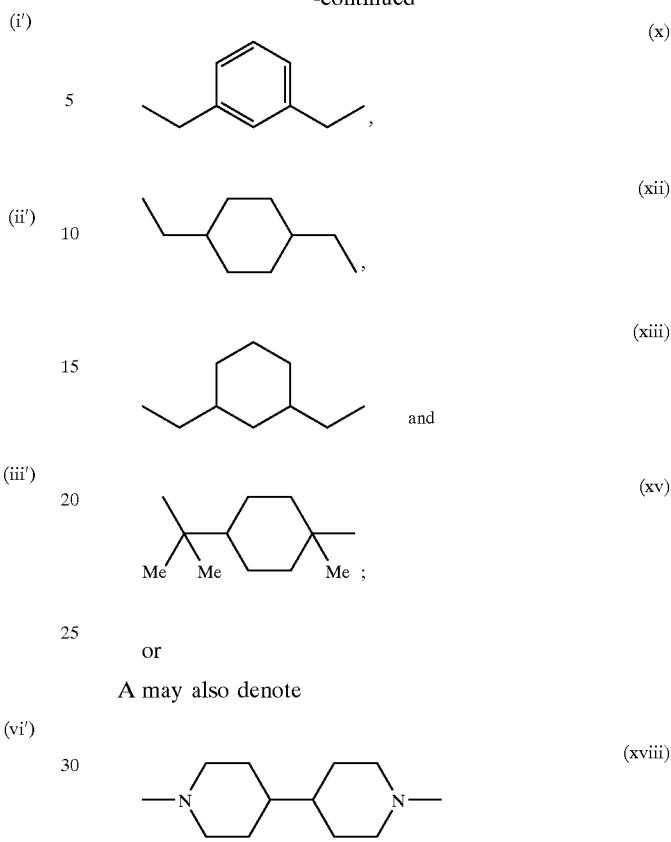

or
A may also denote

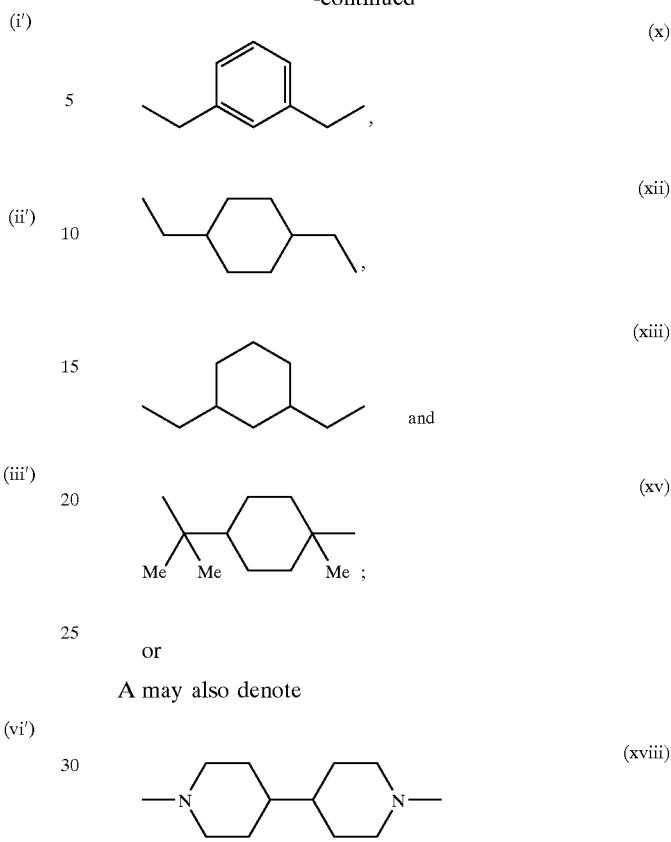

if the grouping B¹—Ar¹—X¹—Ar²—X²— denotes the group (i) and the grouping —X³—Ar³—X⁴—Ar⁴—B² denotes the group (i'), optionally in the form of their racemates, enantiomers, diastereomers, tautomers and mixtures thereof, and optionally the pharmacologically harmless acid addition salts thereof.

Particularly preferred are the compounds of general formula (IA1)

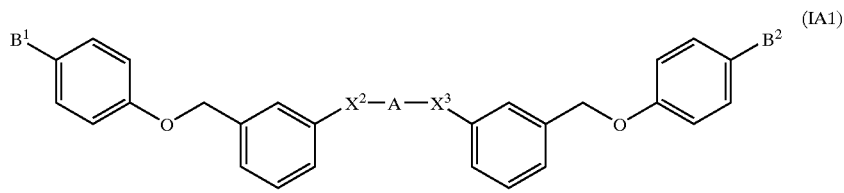

wherein B¹, B², A, X² and X³ have the meanings given hereinbefore and hereinafter, optionally in the form of their racemates, enantiomers, diastereomers, tautomers and mixtures thereof, and optionally the pharmacologically harmless acid addition salts thereof.

Particularly preferred are the compounds of general formula (I), (IA) or (IA1), wherein —X²—A—X³— denotes a group of the formula

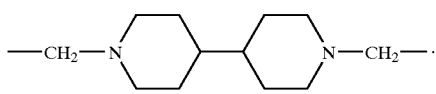

Compounds of general formula (I) wherein $B^1$ and $B^2$ which may be identical or different denote —C(=NR$^1$)—NR$^1$H are so-called prodrugs if neither $R^1$ nor $R^{1'}$ denotes hydrogen. After being taken by the patient these prodrugs can be converted by the body, on the basis of a functionality which can be cleaved in vivo, into the therapeutically active compounds of general formula (I) wherein $B^1$ and $B^2$ which may be identical or different denote —C(=NH)NH$_2$.

The term alkyl groups (including those which are part of other groups) denotes branched and unbranched alkyl groups with 1 to 18 carbon atoms, preferably 1–14, most preferably 1–10 carbon atoms, unless otherwise stated. Examples include methyl, ethyl, propyl, butyl, pentyl, hexyl, heptyl and octyl, etc. Unless otherwise stated, the above terms propyl, butyl, pentyl, hexyl, heptyl and octyl, etc., also include all the possible isomeric forms. For example, the term propyl also includes the two isomeric groups n-propyl and iso-propyl, the term butyl includes n-butyl, iso-butyl, sec. butyl and tert.-butyl, the term pentyl includes iso-pentyl, neopentyl, etc. In some cases common abbreviations are also used to denote the abovementioned alkyl groups, such as Me for methyl, Et for ethyl etc.

Examples of alkylene groups are branched and unbranched alkylene bridges having 1 to 18 carbon atoms, preferably 1–14 carbon atoms, most preferably 1–10 carbon atoms. These include, for example: methylene, ethylene, propylene, butylene, etc. Unless otherwise stated, the above terms propylene, butylene, etc. also include all the possible isomeric forms. For example, the term propylene includes the two isomeric bridges n-propylene and dimethylmethylene, the term butylene includes n-butylene, 1-methylpropylene, 2-methylpropylene, 1.1-dimethylethylene, 1.2-dimethylethylene etc.

The term alkenyl groups (including those which are part of other groups) denotes branched and unbranched alkenyl groups having 2 to 16 carbon atoms, preferably 2 to 10 carbon atoms, most preferably 2 to 6 carbon atoms, if they contain at least one double bond, for example the abovementioned alkyl groups as well, provided that they contain at least one double bond, such as for example vinyl (provided that no unstable enamines or enolethers are formed), propenyl, iso-propenyl, butenyl, pentenyl, hexenyl.

The term alkynyl groups (including those which are part of other groups) denotes branched and unbranched alkenyl groups having 2 to 16 carbon atoms, preferably 2 to 10 carbon atoms, most preferably 2 to 6 carbon atoms, provided that they have at least one triple bond, for example ethynyl, propargyl, butynyl, pentynyl, hexynyl.

In the abovementioned alkyl groups, alkylene groups and alkenyl groups, one or more hydrogen atoms may optionally be substituted by the groups specified in the definitions. By the phrase "several substituted hydrogen atoms" is meant the substitution of at least 2 hydrogen atoms. When the substituent is fluorine all the hydrogen atoms of the alkyl, alkylene and alkenyl groups may optionally be replaced.

Examples of cycloalkyl groups with 3–10 carbon atoms include cyclopropyl, cyclobutyl, cyclopentyl, cyclohexyl, cycloheptyl, cyclooctyl, cyclononyl and cyclodecyl, which may also be substituted by branched or unbranched alkyl having 1 to 4 carbon atoms, hydroxy and/or halogen or as hereinbefore defined.

In the abovementioned cycloalkyl groups one or more hydrogen atoms may optionally be substituted by the groups mentioned in the definitions. By the phrase "several substituted hydrogen atoms" is meant the substitution of at least 2 hydrogen atoms. When the substituent is fluorine all the hydrogen atoms of the cycloalkyl group may optionally be replaced.

Fluorine, chlorine, bromine or iodine is generally referred to as halogen.

The term $C_3$–$C_{10}$-aza-cycloalkyl groups denotes 3- to 10-membered cycloalkyl groups which contain one or two nitrogen atoms. These include, for example, pyrrolidine, imidazolidine, piperidine, piperazine, azepan, diazepans, etc., each of which, unless otherwise specified, may also be substituted by branched or unbranched alkyl with 1 to 4 carbon atoms, hydroxy and/or halogen or as hereinbefore defined.

Examples of 5–10-membered mono- or bicyclic heteroaryl rings in which up to three carbon atoms may be replaced by one or more heteroatoms selected from among oxygen, nitrogen or sulphur include for example furan, thiophene, pyrrole, pyrazole, imidazole, triazole, pyridine, pyridazine, pyrimidine, pyrazine, triazine, oxazole, isoxazole, thiazole, thiadiazole, oxadiazole, wherein each of the abovementioned heterocycles may optionally also be condensed onto a benzene ring and wherein these heterocycles may be substituted as specified in the definitions.

The term $C_6$–$C_{10}$-aryl denotes an aromatic ring system with 6 to 10 carbon atoms, which, unless otherwise stated, may for example carry one or more of the following substituents: $C_1$–$C_6$-alkyl, $C_1$–$C_6$-alkyloxy, halogen, hydroxy, mercapto, amino, alkylamino, dialkylamino, $CF_3$, cyano, nitro, —CHO, —COOH, —COO—$C_1$–$C_6$-alkyl, —S—$C_1$–$C_6$-alkyl. The preferred aryl group is phenyl.

"=O" denotes an oxygen atom linked via a double bond.

In the abovementioned definitions, unless otherwise specified, all the definitions given for the groups —Ar$^1$—, —Ar$^2$—, —Ar$^3$— and —Ar$^4$— should be regarded as two-bonded groups which may be linked to the two adjacent functions in three possible substitution patterns (ortho, meta and para). Meta- and para-substitution are preferred.

In the abovementioned definitions, unless otherwise specified, all the definitions given for the groups —X$^1$—, —X$^2$—, —A—, —X$^3$— and —X$^4$— should be regarded as two-bonded groups which may be linked to the two adjacent functions in two possible orientations. Preferably, —X$^1$— denotes —O—(CH$_2$)$_n$—, —S—(CH$_2$)$_n$— or —NR$^3$—(CH$_2$)$_n$— particularly —O—CH$_2$—; and —X$^4$— denotes —(CH$_2$)$_n$—O—, —(CH$_2$)$_n$—S—or —(CH$_2$)—NR$^3$—$_n$, particularly —CH$_2$—O—.

According to another aspect, the present invention relates to the use of the above-defined compounds of general formula (I) as pharmaceutical compositions. In particular, the present invention relates to the use of the compounds of general formula (I) for preparing a pharmaceutical composition for the prevention and/or treatment of diseases in which tryptase inhibitors may have a therapeutic benefit.

It is preferred according to the invention to use compounds of general formula (I) for the purpose mentioned above, for preparing a pharmaceutical composition for the prevention and/or treatment of inflammatory and/or allergic diseases.

It is particularly preferable to use the compounds of general formula (I) as mentioned above for preparing a pharmaceutical composition for the prevention and/or treatment of bronchial asthma, allergic rhinitis, allergic conjunctivitis, atopic dermatitis, urticaria, allergic otitis, allergic gastro-intestinal disorders, Crohn's disease, ulcerative colitis, anaphylactic shock, septic shock, shock lung (ARDS) and arthritis.

It is also advantageous to use the compounds of general formula (I) as mentioned above for preparing a pharmaceutical composition for the prevention and/or treatment of fibroses such as lung fibrosis, fibrosing alveolitis and scarring, collagenoses such as lupus erythematodes and sclerodermia as well as arteriosclerosis, psoriasis and neoplasm.

One possible method of obtaining the compounds of general formula (I) according to the invention with the aid of and using conventional chemical methods of synthesis is diagrammatically shown hereinafter.

Method A

In order to prepare compounds of general formula (I)

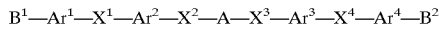

wherein $B^1$ and $B^2$ denote —C(=NH)—NH$_2$, imidoesters of general formula (II)

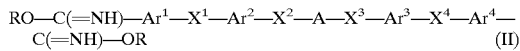

wherein R denotes $C_1$-$C_6$-alkyl, are reacted with ammonia.

The reaction is preferably carried out in an organic solvent at temperatures between about 0° C. and the boiling temperature of the reaction mixture, preferably between ambient temperature and about 100° C. or the boiling temperature of the solvent used, if this is lower. Suitable solvents are polar organic solvents, preferably alcohols, most preferably methanol, ethanol or propanols. If the starting materials are sufficiently acid-stable the reaction may take place via the corresponding acid imide chlorides instead of via the imidoesters.

Method B1

In order to prepare compounds of general formula (I)

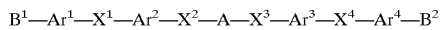

wherein $B^1$ and $B^2$ denote —C(=NOH)—NH$_2$, compounds of general formula (III)

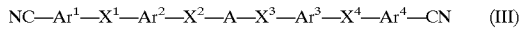

are treated with hydroxylamine in the presence of carbonates or alkoxides of the alkali or alkaline earth metals in solvents such as methanol, ethanol, n-propanol or isopropanol, possibly in admixture with dioxan or tetrahydrofuran. The alkoxides may be prepared from the alkali metals or metal hydrides and the corresponding alcohol. The reaction is preferably carried out at 20–100° C., most preferably at the boiling temperature of the solvent used.

Method B²

In order to prepare compounds of general formula (I)

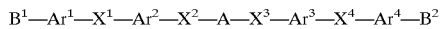

wherein $B^1$ and $B^2$ denote —C(=NH)—NH$_2$, amidoximes of general formula (I) wherein $B^1$ and $B^2$ denote —C(=NOH)—NH$_2$ are reduced.

Catalytic hydrogenation is suitable for the reduction, particularly with Raney nickel, palladium or platinum in a lower alcohol, e.g. methanol, ethanol or propanols. Appropriately the amidoxime is dissolved in a polar solvent, e.g. methanol, ethanol, propanols, tetrahydrofuran or dimethylformamide, with the addition of the calculated amount of the acid whose salt is desired as the end product, and hydrogenated at ambient temperature under gentle pressure from 1 bar, e.g. at 5 bar, until the uptake of hydrogen has ceased.

Method C

In order to prepare compounds of general formula (I)

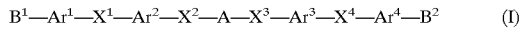

wherein $B^1$ and $B^2$ denote —C(=NH)—NH$_2$, compounds of general formula (III)

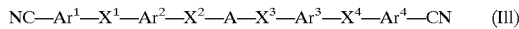

are reacted with Li-hexamethyldisilazane. Suitable solvents for the reaction are nonpolar and polar aprotic solvents such as for example toluene, ether or tetrahydrofuran at temperatures of −80° C. to 120° C. To cleave the silyl groups inorganic and organic acids are used such as HCl, HBr, H$_2$SO$_4$, sulphonic acids such as p-toluenesulphonic acid, benzenesulphonic acid or methanesulphonic acid, carboxylic acids such as formic acid, acetic acid or trifluoroacetic acid at temperatures of 0° C. to 100° C.

Method D

In order to prepare compounds of general formula (I)

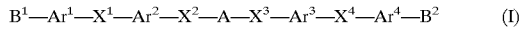

wherein $B^1$ and $B^2$ may have the meanings given hereinbefore, compounds of general formula (IV and (V)

wherein PG may denote a protecting group suitable for protecting amines, which may also be present twice, are reacted with a diamine with subsequent reduction of the C=N— double bonds thus formed. Suitable amino protecting groups PG which may be mentioned here include for example alkoxycarbonyl, particularly tert-butyloxycarbonyl, benzyloxycarbonyl, 2-trimethylsilylethyloxycarbonyl, 2,2,2-trichloroethyloxycarbonyl etc. For the reaction, aldehydes of formula (IV) and (V) are reacted with diamines in aprotic solvents such as toluene, dichloromethane, ethyl acetate, ether, tetrahydrofuran etc. at temperatures of −80° C. to 120° C. The subsequent reduction may be carried out with complex hydrides such as for example LiAlH$_4$, Li-alkoxyhydrides, NaBH$_4$, NaBHCN$_3$, NaBH(OAc)$_3$, etc.

For the reaction with primary amines NaBH$_4$ is preferably used, while for secondary amines NaBH(OAc)$_3$ is preferred. The solvents used may be polar solvents such as DMF, alcohols such as methanol, ethanol, propanols etc. and water. The temperature is kept in a range from −30° C. to 100° C. For cleaving the hydride complexes, organic and inorganic acids are used, such as HCl, HBr, H$_2$SO$_4$, formic acid, acetic acid, sulphonic acids such as p-toluenesulphonic acid, benzenesulphonic acid or methanesulphonic acid in polar solvents such as ethyl acetate, methanol, ethanol, propanols, water, DMF, acetonitrile. Finally, the protecting groups are cleaved, particularly with inorganic or organic acids or by hydrogenolysis or using other methods known from the prior art which are conventionally used for cleaving specific protecting groups.

Method E

In order to prepare compounds of general formula (I)

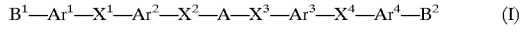

wherein $B^1$ and $B^2$ may have the meanings given hereinbefore, compounds of general formula (VI) and (VII)

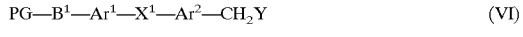

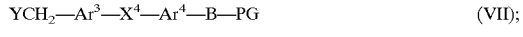

wherein PG may denote a protecting group used to protect amines, which may also be present twice and Y denotes fluorine, chlorine, bromine or iodine or a $C_1$–$C_4$-alkyl— or an arylsulphonate group are reacted with a diamine or a dialcohol. Suitable amino protecting groups PG which may be mentioned here include for example alkoxycarbonyl, particularly tert-butyloxycarbonyl, benzyloxycarbonyl, 2-trimethyl-silylethyloxycarbonyl, 2,2,2-trichloroethyloxycarbonyl etc.

The reaction is carried out with basic adjuvants such as for example alkali metal or alkaline earth metal hydroxides, alkali metal or alkaline earth metal carbonates, $C_1$–$C_4$-alkali metal alkoxides in solvents which are inert under the reaction conditions used, such as formamides—preferably dimethylformamide (DMF)—, $C_1$–$C_4$-alkyl esters of carboxylic acids—preferably ethyl acetate or ethyl formate—, aromatic or aliphatic hydrocarbons—preferably toluene—or in branched or unbranched $C_1$–$C_4$-alcohols.

In the final reaction step, the protecting groups are cleaved, particularly with inorganic or organic acids or by hydrogenolysis or using other methods known from the prior art which are conventionally used for cleaving specific protecting groups.

Method F

In order to prepare compounds of general formula (I)

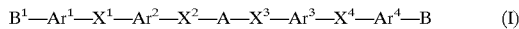
$$B^1\text{—}Ar^1\text{—}X^1\text{—}Ar^2\text{—}X^2\text{—}A\text{—}X^3\text{—}Ar^3\text{—}X^4\text{—}Ar^4\text{—}B \quad (I)$$

wherein $B^1$ and $B^2$ denote —C(=NR$^1$)—NH$_2$ with $R^1 \neq H$, compounds of general formula (I), wherein $B^1$ and $B^2$ wherein $B^1$ and $B^2$ denote —CH$_2$—NH$_2$, the corresponding nitrile compounds of general formula (III)

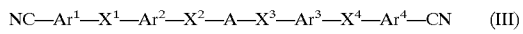
$$NC\text{—}Ar^1\text{—}X^1\text{—}Ar^2\text{—}X^2\text{—}A\text{—}X^3\text{—}Ar^3\text{—}X^4\text{—}Ar^4\text{—}CN \quad (III)$$

are reduced, either by catalytic hydrogenation in solvents such as methanol, ethanol, higher alcohols, DMF or water, with catalysts such as Raney nickel, Pd/C, platinum, or with hydride reagents, such as NaBH$_4$, Ca(BH$_4$)$_2$, LiAlH$_4$ and other Al— or B-hydrides at temperatures of 0–100° C. and pressures of 760 Torr or more.

The abovementioned methods A–G are suitable for synthesising both symmetrical and non-symmetrical compounds of general formula (I).

Some methods of preparing the compounds of general formula (I) according to the invention are described in more detail hereinafter, by way of example. The Examples which follow serve only as a detailed illustration, without restricting the subject of the invention.

EXAMPLE 1

(Method B1):

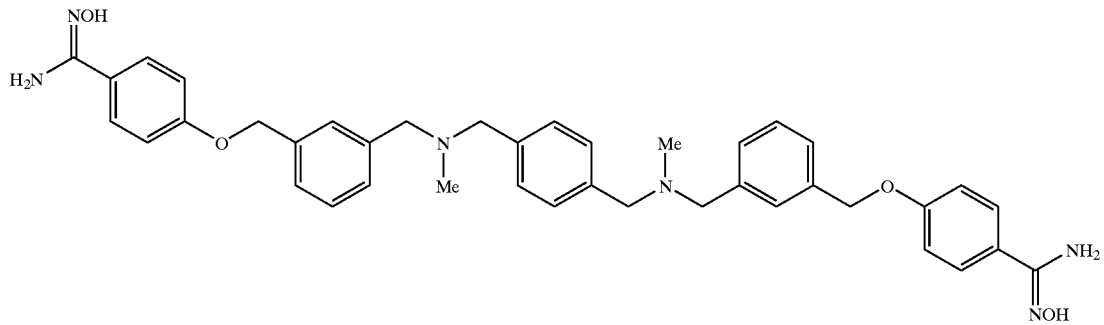

denote —C(=NH)—NH$_2$, are reacted with chloroformates or acyl halides or corresponding anhydrides. For this, the bis-benzamidines in solvents such as toluene, ether, dichloromethane, DMF, ethyl acetate, water at temperatures of 0° C. to 120° C. are combined with acyl halides or acid anhydrides, with the addition of a basic substance such as triethylamine, cyclic amines such as DBU, or pyridine. The amines may also be used as solvents. Two-phase mixtures such as e.g. water/toluene or water/dichloromethane are also suitable for the reaction.

The compounds of formula (I) wherein $B^1$ and $B^2$ denote —C(=NR$^1$)—NH$_2$ (with $R^1 \neq H$) may also be prepared from the acylated amidines (IV) and (V) according to Method D and E. In this case the group $R^1$ acts as the protecting group PG. There is no need here to cleave the protecting group PG as mentioned in Method D and E.

Method G

In order to prepare compounds of general formula (I)

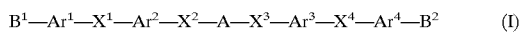
$$B^1\text{—}Ar^1\text{—}X^1\text{—}Ar^2\text{—}X^2\text{—}A\text{—}X^3\text{—}Ar^3\text{—}X^4\text{—}Ar^4\text{—}B^2 \quad (I)$$

1.4 g of sodium carbonate and 1.83 g of hydroxylamine xHCl in 10 ml H$_2$O were added dropwise to 2.3 g of the corresponding dinitrile in 80 ml of ethanol and refluxed for 3 h. The suspension formed was suction filtered and washed with ethanol. The crystals were chromatographed over silica gel 60 with acetonitrile/dichloromethane/formic acid/H$_2$O 70:20:15:10. After conversion into the base with 2N NaOH and extracting with ethyl acetate, the substance was suspended in methanol and combined with dilute methanesulphonic acid. The solution was concentrated and slowly crystallised with ether. 0.7 g were obtained in the form of the trimethanesulphonate. M.p. 210–212° C.

$^1$H-NMR(250 MHz, DMSO-d6):δ=9.66(2H, s, OH); 7.84–7.07 (2OH, m, aryl-H); 5.75 (4H, s, NH$_2$), 5.12 (4H, s, OCH$_2$—); 3.57; 3.55 (8H, 2s, N—CH$_2$—); 2.36 (6H, s, N—CH$_3$); 2.11 (9H, s, CH$_3$—C=O).

EXAMPLE 2

(Method C):

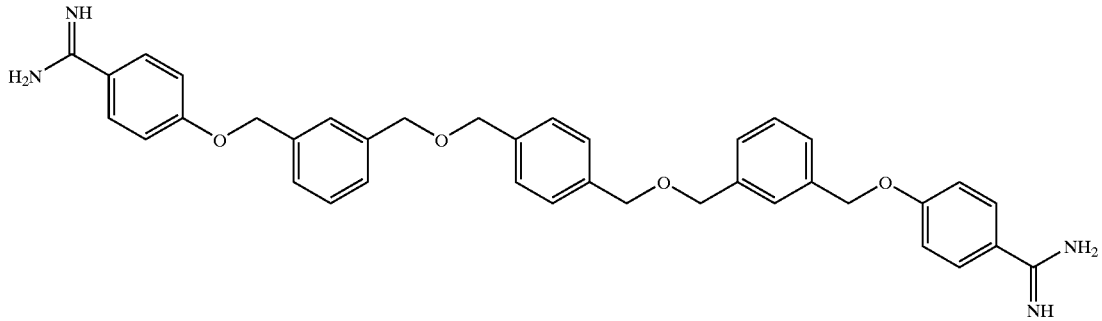

1.74 g of the corresponding dinitrile were dissolved in 75 THF and 20 ml of lithium hexamethyldisilazane (1M) in THF were added dropwise under nitrogen. After the addition of another 25 ml of THF and heating to 45° C., the solution was stirred for 12 h at ambient temperature. 18 ml of 4N hydrochloric acid were slowly added dropwise with cooling at 0° C. The THF was distilled off, water was added and the crystals were suction filtered and washed with water. The dihydrochloride was converted into the base with 2N NaOH in DMF. This base was chromatographed over 160 g of silica gel 60 (acetonitrile/chloroform/glacial acetic acid/water: 75:20:10:7.5).

Yield: 0.73 as the diacetate. M.p.: 221° C.

$^1$H-NMR(250 MHz, DMSO-d6):δ=9.92 (8H, broad, —C(=NH$_2$$^+$)NH$_2$); 8.03–7.25 (20H, m, aryl-H); 5.33 (4H, s, OCH$_2$—); 4.64; 4.63 (8H, 2s, —CH$_2$—O—CH$_2$—); 1.74 (6H, s, CH$_3$—C=O).

EXAMPLE 3

(Method D):

0.49 g of diaminoethane in 2 ml dichloromethane were taken and 0.8 g of 3-[4-(N-Boc-aminomethyl)-phenyloxymethyl]-benzaldehyde (70%) were added. After heating to 80° C. and cooling, 10 ml of ethanol were added and the solution was combined with 100 mg of NaBH$_4$ at 0–5° C. After 12 h at ambient temperature, the mixture was acidified with 1 ml of 2N HCl at 0–5° C. and after 2 h the precipitated crystals were suction filtered. After dissolving in HCl/ethyl acetate, DMF and methanol, the mixture was heated and after 12 h evaporated down. The residue was taken up in methanol and the crystals were suction filtered.

Yield: 0.33 g.

$^1$H-NMR(250 MHz, CD$_3$OD):δ=7.75–7.10 (16H, m, aryl-H); 5.19 (4H, s, OCH$_2$—); 4.32(4H, s, N—CH$_2$-phenyl); 4.09 (4H, s, CH$_2$NH$_2$); 3.47 (4H, s, N—CH$_2$CH$_2$—N).

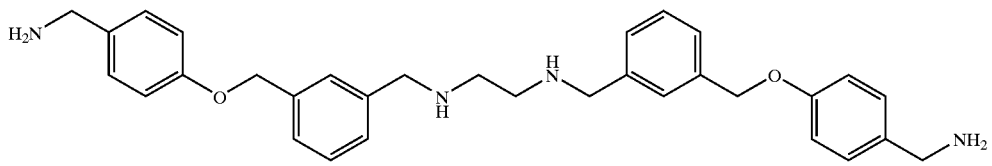

EXAMPLE 4

(Method E):

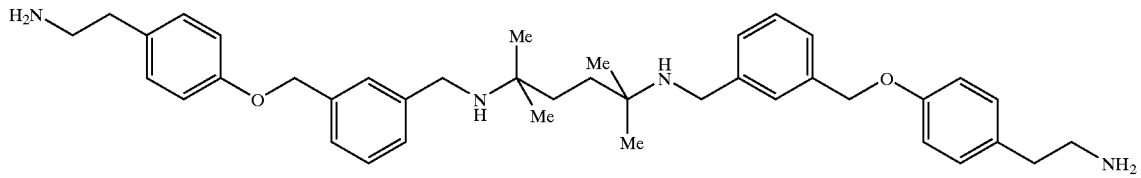

3.75 g of N-Boc-2-[4-(3-chlormethyl-benzyloxy-)phenyl]ethylamine, 0.72 g of 2,5-diamino-2,5-dimethyl-hexane, 1.4 g of potassium carbonate and 0.1 g of potassium iodide in 15 ml of DMF were stirred for 6 h at an internal temperature of 75° C. and for a further 7 h at 140° C. The suspension was evaporated down, the residue was taken up in water and extracted with ethyl acetate. The organic phase dried over $Na_2SO_4$ was evaporated down and the residue was chromatographed over silica gel 60 with dichloromethane/methanol/conc. ammonia 65:35:5. The Boc-protected compound was dissolved in 10 ml of ethyl acetate and mixed with 10 ml of 3M HCl in ethyl acetate and stirred for 24 h. The crystals precipitated were recrystallised from 50 ml of ethanol. Yield: 0.22 g in the form of the tetrahydrochloride. M.p.: 270° C. (decomposition).

$^1$H-NMR(250 MHz, $CD_3OD$):δ=7.85–6.98 (16H, m, aryl-H); 5.16 (4H, s, $OCH_2$—); 4.30 (4H, s, N—$CH_2$-phenyl); 3.15; 2.90 (8H, 2m, N—$CH_2$—$CH_2$-phenyl); 1.95 (4H, s, C—$CH_2CH_2$—); 1.52 (12H, s, $CH_3$—C—$CH_3$).

EXAMPLE 5

(Method F):

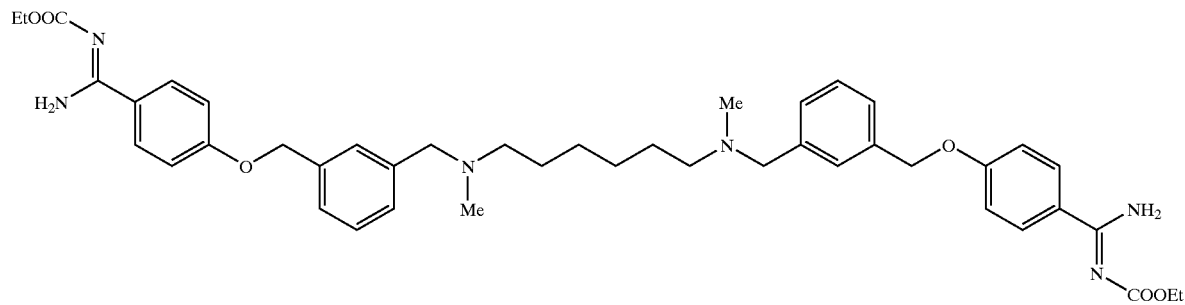

0.3 g of the corresponding bis-benzamidine were dissolved as the base in a little absolute ethanol. 50 ml of dichloromethane and 0.115 g of ethyl chloroformate were added thereto and at ambient temperature 1 ml of triethylamine was added dropwise. After 2 h the mixture was extracted twice with 50 ml of water. The organic phases were evaporated down and chromatographed over silica gel 60 (acetonitrile/dichloromethane/formic acid/$H_2O$ 70:20:15:10). The product was taken up in water, combined with sodium hydroxide solution, extracted with 100 ml of ethyl acetate, dried and evaporated down.

Yield: 85 mg in the form of a colourless oil.

$^1$H-NMR(250 MHz, $CDCl_3$):δ=8.50 (4H, s, $NH_2$); 8.02–6.96 (16H, m, aryl-H); 5.18 (4H, s, $OCH_2$—); 4.25 (4H, qu, J=7.0 HZ, $OCH_2$—$CH_3$); 4.10 (4H, s, N—$CH_2$-phenyl); 2.80–1.07 (12H, m, N—$CH_2(CH_2)_4$—$CH_2$—N); 2.55 (6H, s, N—$CH_3$); 1.28 (6H, t, J=7.0 HZ, $OCH_2$—$CH_3$).

EXAMPLE 6

(Method G):

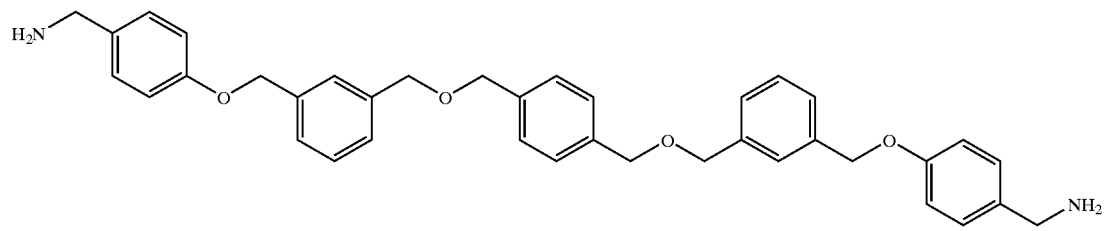

1.16 g of the corresponding dinitrile in 60 ml DMF were hydrogenated with the addition of methanolic ammonia solution and Raney nickel for 6 h at 5 bar and 60° C. The catalyst was removed by suction filtering and the solvent was eliminated. The residue was dissolved while hot in 100 ml of DMF and after cooling down the solution was suction filtered. The filtrate was dissolved in 50 ml of DMF, the calculated amount of ethereal hydrochloric acid was added, the solvent was distilled off and stirred with ethanol. The residue was converted into the base using conc. ammonia and chromatographed over 70 g of silica gel 60 (acetonitrile/chloroform/glacial acetic acid/water 75:20:10:7.5).

Yield: 0.24 g in the form of the diacetate. M.p.: 148° C.

$^1$H-NMR(250 MHz, DMS0-d6):δ=7.44–6.86 (2OH, m, aryl-H); 5.08 (4H—OCH$_2$—); 4.60 (6H, s, CH$_3$); 4.52; 4.51 (8H, 2s, —CH$_2$—O—CH$_2$—); 3.69 (4H, s, CH$_2$—NH$_2$); 1.81 (6H, s, CH$_3$—C=O).

The following compounds, inter alia, were also obtained analogously to the examples of synthesis described above and according to synthesis methods A–G:

EXAMPLE 7
(Method G):

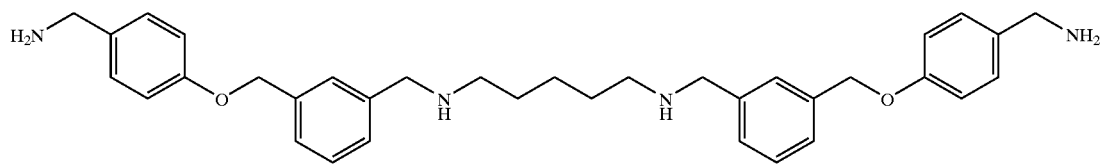

$^1$H-NMR(250 MHz, CD$_3$OD):δ=7.72–7.07 (16H, m, aryl-H); 5.20 (4H, s, OCH$_2$); 4.25 (4H, s, N—CH$_2$-phenyl); 4.10 (4H, s, CH$_2$—NH$_2$); 3.09 (4H, m, N—CH$_2$(CH$_2$)$_3$—CH$_2$—N); 1.89–1.40 (6H, m, N—CH$_2$(CH$_2$)—).

EXAMPLE 8
(Method D):

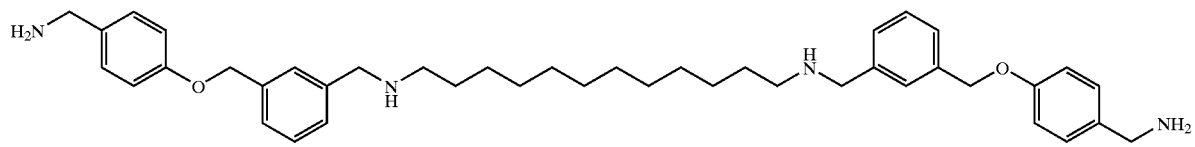

$^1$H-NMR(250 MHz, CD$_3$OD):δ=7.62–7.02 (16H, m, aryl-H); 5.14 (4H, s, OCH$_2$—); 4.20 (4H, s, H—CH$_2$-phenyl); 4.06 (4H, s, CH$_2$—NH$_2$); 2.99 (4H, m, N—CH$_2$—(CH$_2$)$_{10}$—CH$_2$—N); 1.82–1.17 (20H, m, N—(CH$_2$)$_{10}$—).

EXAMPLE 9
(Method D):

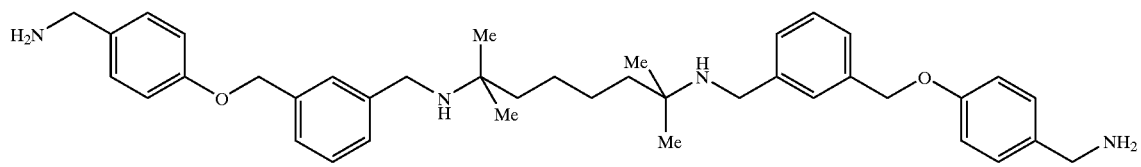

¹H-NMR(250 MHz, CD₃OD):δ=7.93–7.19 (16H, m, aryl-H); 5.28 (4H, s, OCH₂—); 4.33 (4H, s, N—CH₂-phenyl); 4.13 (4H, s, CH₂—NH₂); 2.03–1.38 (8H, m, C—(CH₂)₄—C); 1.48 (12H, s, C—(CH₃)₂).

EXAMPLE 10
(Method D):

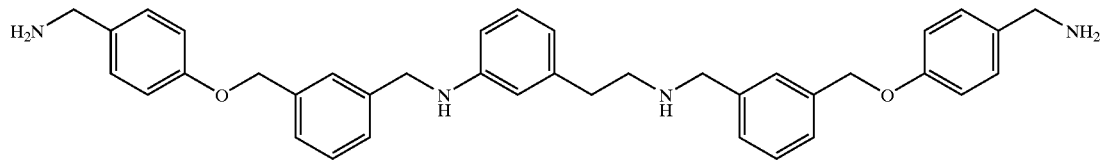

¹H-NMR(250 MHz, CD₃OD):δ=7.63–6.85 (20H, m, aryl-H); 5.10; 5.04(4H, 2s, OCH₂); 4.40; 4.18; 4.01 (8H, 3s, N—CH₂); 3.20; 2.95 (4H, 2m, H—CH₂CH₂—N).

EXAMPLE 11
(Method D):

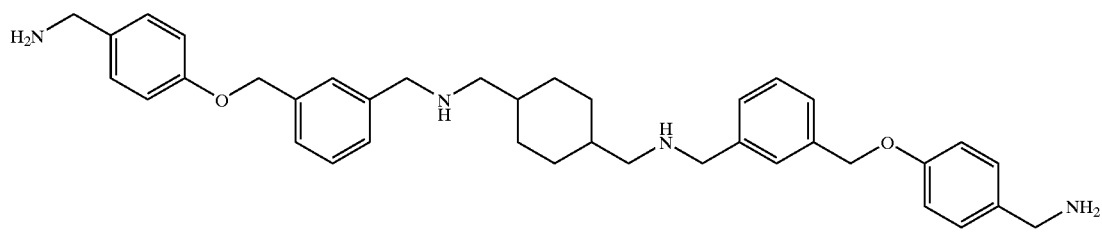

¹H-NMR(250 MHz, CD₃OD):δ=7.70–7.03 (16H, m, aryl-H); 5.15 (4H, s, OCH₂—); 4.20 (4H, s, N—CH₂-phenyl); 4.05 (4H, s, CH₂—NH₂); 2.82 (4H, d, J=5.8 Hz, CH₂—CH); 2.00–0.95 (10H, m, cyclohexyl-H).

EXAMPLE 12
(Method D):

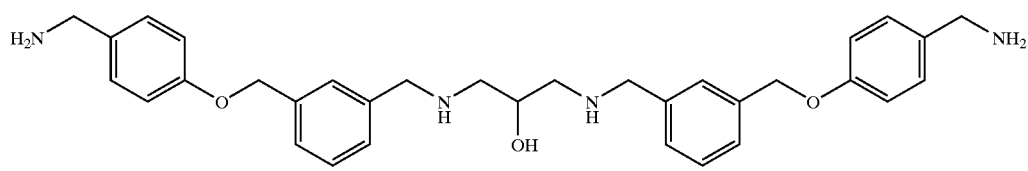

¹H-NMR(250 MHz, CD₃OD):δ=7.76–7.07 (16H, m, aryl-H); 5.19 (4H, s, OCH₂); 4.37 (1H, m, CH-OH); 4.29 (4H, s, N—CH₂-phenyl); 4.09 (4H, s, CH₂—MH₂); 3.16 (4H, m, —CH₂—CHOH—CH₂—).

EXAMPLE 13
(Method D):

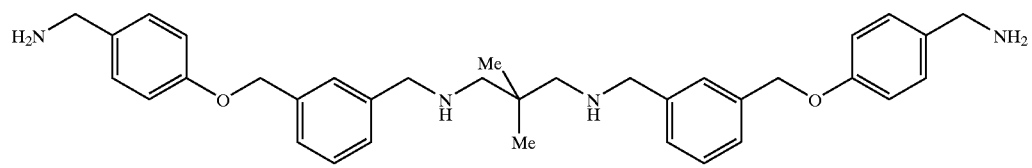

$^1$H-NMR(250 MHz, CD$_3$OD):δ=7.70–7.05 (16H, m, aryl-H); 5.15 (4H, s, OCH$_2$); 4.23 (4H, s, N—CH$_2$-phenyl); 4.07 (4H, s, CH$_2$—NH$_2$); 3.02 (4H, S, —CH$_2$—C—CH$_2$—); 1.11 (6H, s, CH$_3$—C—CH$_3$).

EXAMPLE 14

(Method D):

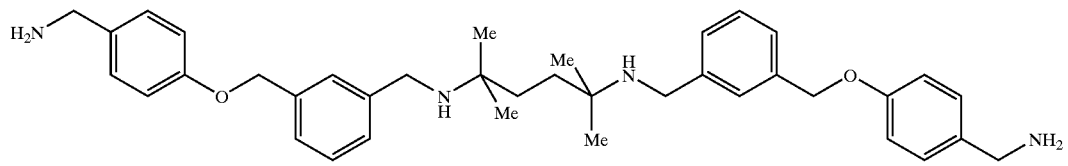

$^1$H-NMR(250 MHz, CD$_3$OD):δ=7.88–7.17 (16H, m, aryl-H); 5.27 (4H, s, OCH$_2$); 4.31 (4H, s, N—CH$_2$-phenyl); 4.13 (4H, s, CH$_2$—NH$_2$); 1.93 (4H, s, C—CH$_2$CH$_2$—C); 1.51 (12H, s, CH$_3$—C—CH$_3$).

EXAMPLE 15

(Method D):

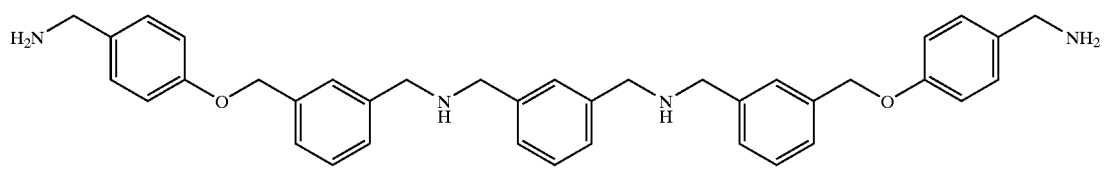

$^1$H-NMR(250 MHz, CD$_3$OD):δ=7.79–7.13 (2OH, m, aryl-H; 5.22 (4H, s, OCH$_2$); 4.28 (8H, s, N—CH$_2$-phenyl); 4.11 (4H, s, CH$_2$—NH$_2$).

EXAMPLE 16

(Method D):

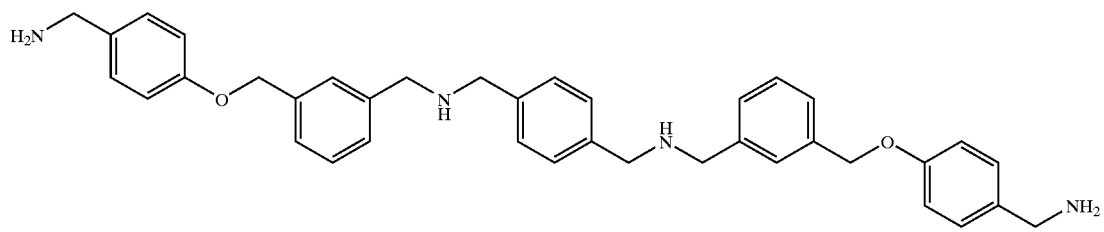

$^1$H-NMR(250 MHz, CD$_3$OD):δ=7.60–7.00 (2OH, m, aryl-H); 5.14 (4H, s, OCH$_2$); 4.15 (8H, s, N—CH$_2$-phenyl); 4.04 (4H, s, NH$_2$—CH$_2$).

EXAMPLE 17

(Method D):

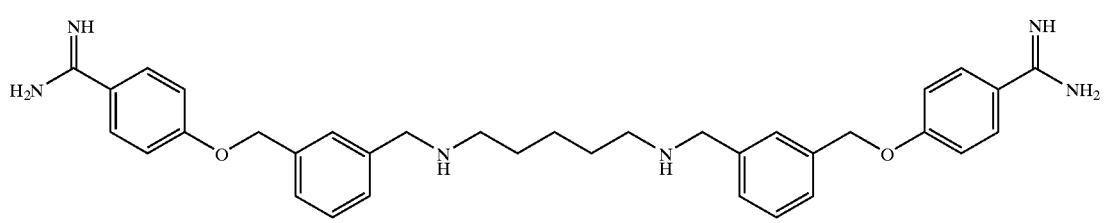

¹H-NMR(250 MHz, DMSO-d6):δ=9.54 (4H, s, NH₂⁺); 9.23; 9.09 (8H, 2s, —C(=NH₂⁺)NH₂); 7.90–7.15 (16H, m, aryl-H); 5.22 (4H, s, OCH₂); 4.11 (4H, N—CH₂-phenyl); 2.83 (4H, m, N—CH₂(CH₂)₃—CH₂—N); 1.54–0.90 (6H, m, N—CH₂—(CH₂—).

EXAMPLE 18
(Method D):

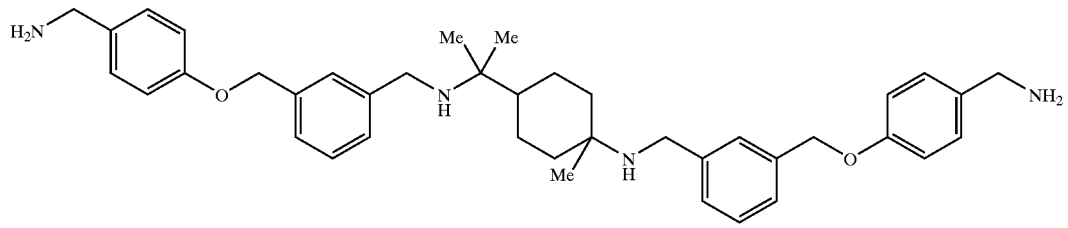

¹H-NMR(250 MHz, CD₃OD):δ=7.89–7.20(16H, m, aryl-H); 5.28 (4H, s, OCH₂); 4.39; 4.33 (4H, 2s, N—CH₂-phenyl); 4.15 (4H, s, CH₂—NH₂); 2.43–1.30 (9H, m, cyclohexyl); 1.56 (3H, s, C—CH₃); 1.50 (6H, s, CH₃—C—CH₃).

EXAMPLE 19
(Method D):

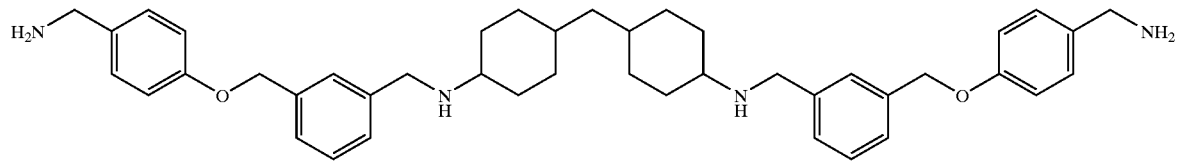

¹H-NMR(250 MHz, CD₃OD):δ=7.68–6.93 (16H, m, aryl-H); 5.08 (4H, s, OCH₂); 4.19 (4H, s, N—CH₂-phenyl); 4.02 (4H, s, CH₂—NH₂); 3.08 (2H, m, N—CH-cyclohexyl); 2.30–0.88 (20H, cyclohex-CH₂-cyclohex-H).

EXAMPLE 20
(Method D):

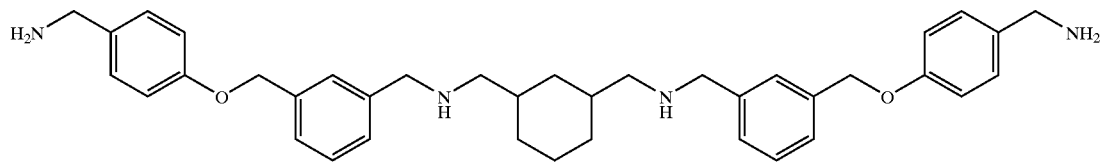

¹H-NMR(250 MHz, CD₃OD):δ=7.85–7.13 (16H, m, aryl-H); 5.23 (4H, s, OCH₂); 4.31 (4H, s, N—CH₂-phenyl); 4.11 (4H, s, CH₂—NH₂); 3.12 (4H, m, N—CH₂-cyclohexyl); 2.33–0.73 (10H, m, cyclohexyl-H).

EXAMPLE 21
(Method D):
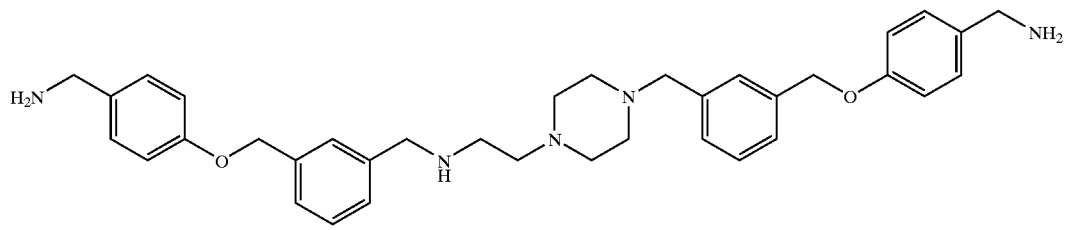
¹H-NMR(250 MHz, CD₃OD):δ=7.93–7.15 (16H, m, aryl-H); 5.28 (4H, s, OCH₂); 4.35 (4H, s, N—CH₂-phenyl); 4.14 (4H, m, CH₂—NH₂); 3.76–3.46 (12H, m, NCH₂CH₂-pip.).
EXAMPLE 22
(Method D):
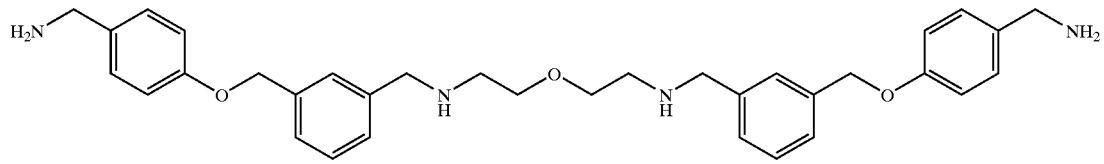
¹H-NMR(250 MHz, DMSO-d6):δ=9.54 (4H, s, NH₂); 9.23; 9.09 (8H, 2s, C(=NH₂NH₂⁺)NH₂); 7.90–7.15 (16H, m, aryl-H); 5.22 (4H, s, OCH₂); 4.11 (4H, N—CH₂-phenyl); 2.83 (4H, m, N—CH₂(CH₂)₃—CH₂—N); 1.54–0.90 (6H, m, N—CH₂—(CH₂)₃—).
EXAMPLE 23
(Method D):
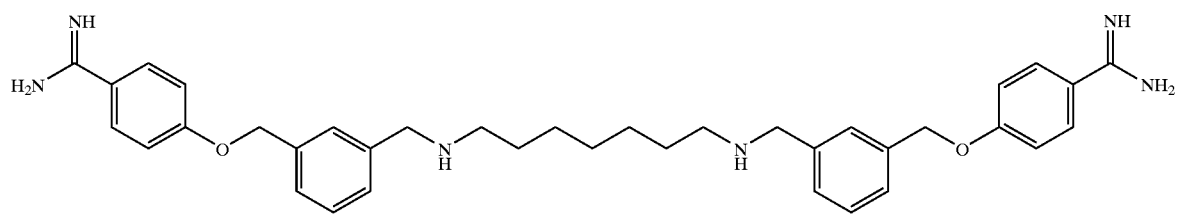
¹H-NMR(250 MHz, CD₃OD):δ=7.88–7.16 (16H, m, aryl-H); 5.27 (4H, s, OCH₂); 4.24 (4H, s, N—CH₂-phenyl); 3.05 (4H, m, N—CH₂—(CH₂)₅—CH₂—N—); 1.89–1.27 (1OH, m, N—CH₂(CH₂)₅—).

EXAMPLE 24
(Method D):
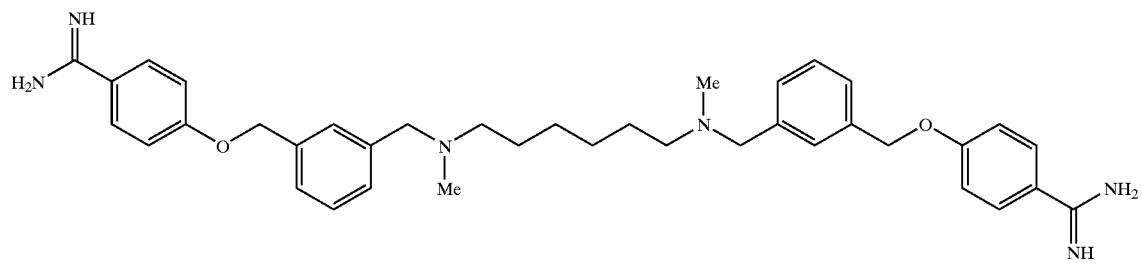
$^1$H-NMR(250 MHz, CD$_3$OD):δ=7.85–7.15 (16H, m, aryl-H); 5.27 (4H, s, OCH$_2$—); 4.51; 4.29 (4H, m, N—CH$_2$-phenyl); 3.20 (4H, m, N—CH$_2$—(CH$_2$)$_4$—CH$_2$—N); 2.81 (6H, s, N—CH$_3$); 2.03–1.35 (8H, m, N—CH$_2$—(CH$_2$)$_4$—).
EXAMPLE 25
(Method D):
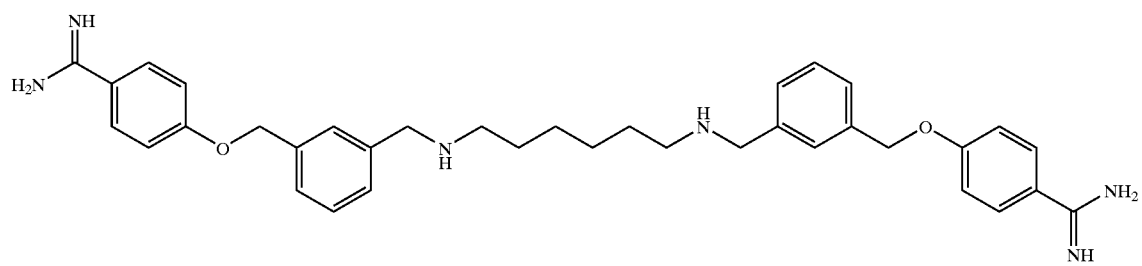
$^1$H-NMR(250 MHz, CD$_3$OD):δ=7.98–7.26 (16H, m, aryl-H); 5.32 (4H, s, OCH$_2$—); 4.28 (4H, s, N—CH$_2$-phenyl); 3.08 (4H, m, N—CH$_2$—(CH$_2$)$_4$—CH$_2$-N); 1.89–1.32 (8H, m, N—CH$_2$—(CH$_2$)$_4$—).
EXAMPLE 26
(Method D):
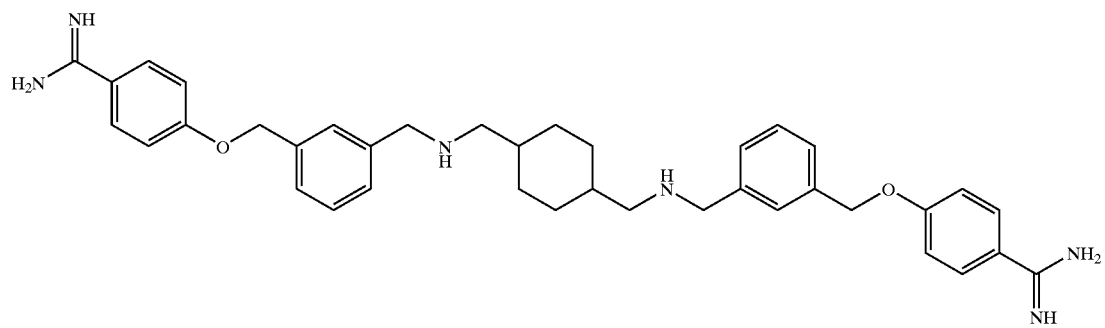
$^1$H-NMR(250 MHz, CD$_3$OD):δ=7.80–7.13 (16H, m, aryl-H); 5.22 (4H, s, OCH$_2$); 4.22 (4H, s, N—CH$_2$-phenyl); 2.90 (4H, d, J=7.4 Hz, N—CH$_2$-cyclohexyl); 2.13–0.93 (10H, m, cyclohexyl-H).

EXAMPLE 27
(Method D):
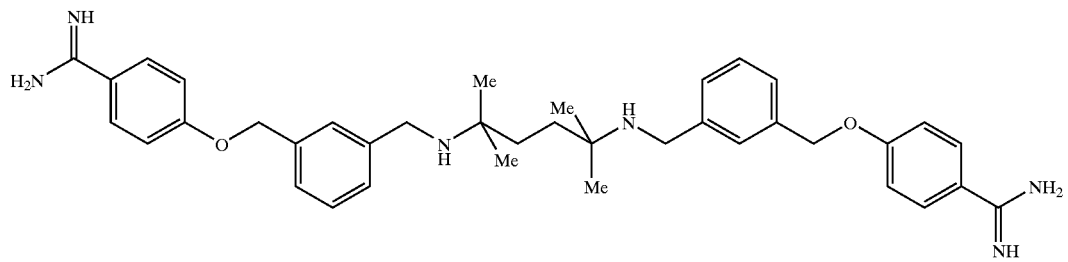
$^1$H-NMR(250 MHz, DMSO-d6):δ=10.15; 9.20; 8.37 (12H, 3s, NH$_2$); 7.99–7.11 (16H, m, aryl-H); 5.22 (4H, s, OCH$_2$—); 4.00 (4H, s, N—CH$_2$-phenyl); 1.91–1.12 (4H, m, —C—CH$_2$CH$_2$—C); 1.30 (12H, s, —C(CH$_3$)$_2$—CH$_2$—CH$_2$—C(CH$_3$)$_2$—).
EXAMPLE 28
(Method D):
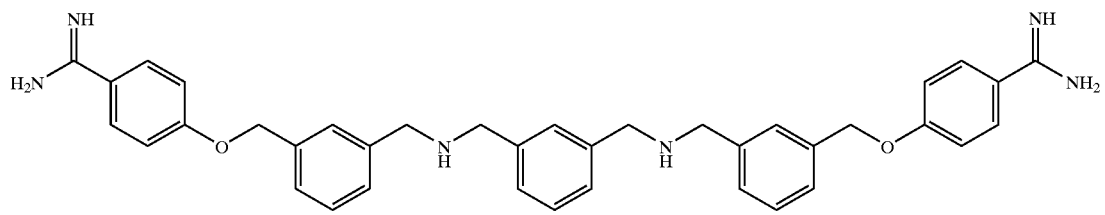
$^1$H-NMR(250 MHz, CD$_3$OD):δ=8.03–7.23 (20H, m, aryl-H); 5.33 (4H, s, OCH$_2$); 4.31 (8H, s, N—CH$_2$-phenyl).
EXAMPLE 29
(Method D):
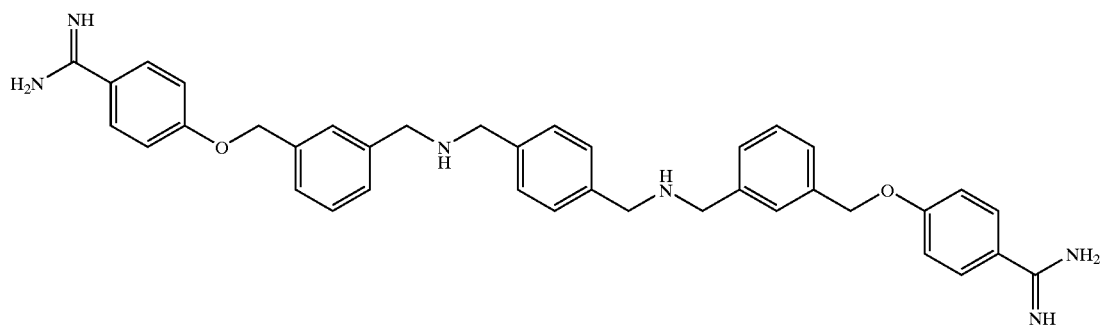
$^1$H-NMR(250 MHz, CD$_3$OD):δ=8.03–7.29 (20H, m, aryl-H); 5.37 (4H, s, OCH$_2$); 4.40 (8H, s, N—CH$_2$-phenyl).

EXAMPLE 30
(Method D):

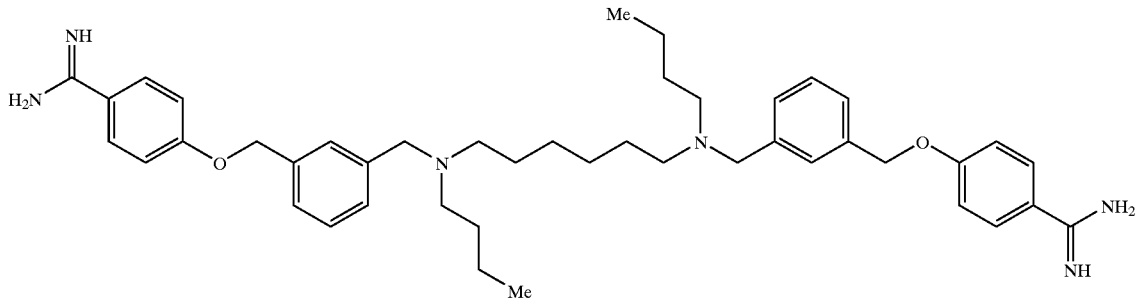

$^1$H-NMR(250 MHz, CD$_3$OD):δ=7.96–7.19 (16H, m, aryl-H); 5.32 (4H, s, OCH$_2$—); 4.43; 4.41 (4H, m, N—CH$_2$-phenyl); 3.15 (8H, m, N—CH$_2$—(CH$_2$—)$_4$—CH$_2$—N; N—CH$_2$—CH$_2$CH$_3$); 2.03–1.22 (16H, m, N—CH$_2$—(CH$_2$)$_4$; N—CH$_2$CH$_2$CH$_2$CH$_3$); 0.95 (6H, m, N—(CH$_2$)$_3$—CH$_3$).

EXAMPLE 31
(Method D):

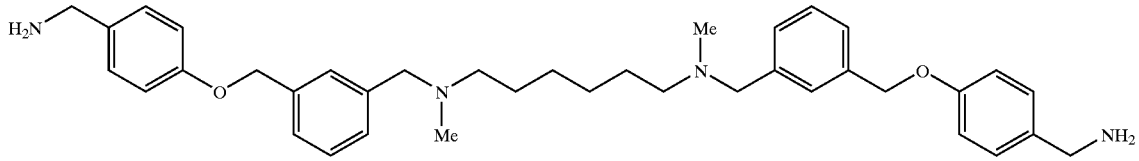

$^1$H-NMR(250 MHz, CD$_3$OD):δ=7.74–7.00 (16H, m, aryl-H); 5.17 (4H, s, OCH$_2$—); 4.40 (4H, s, N—CH$_2$-phenyl); 4.05 (4H, s, CH$_2$—NH$_2$); 3.18 (4H, m, N—CH$_2$(CH$_2$)$_4$—CH$_2$—N); 2.77 (6H, s, N—CH$_3$); 1.95–1.36 (8H, m, N—CH$_2$(CH$_2$)$_4$).

EXAMPLE 32
(Method D):

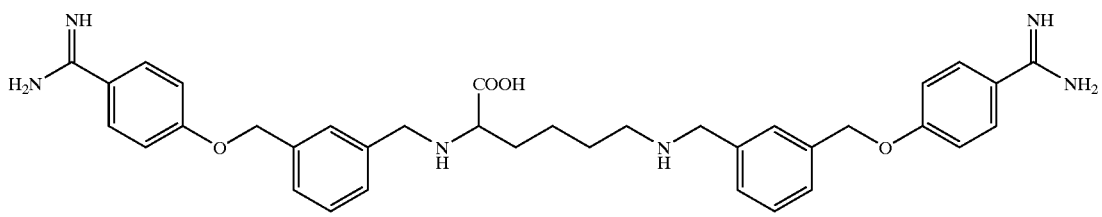

$^1$H-NMR(250 MHz, CD$_3$OD):δ=7.91–7.10 (16H, m, aryl-H); 5.23 (4H, s, OCH$_2$—); 4.24 (4H, s, N—CH$_2$-phenyl); 2.86 (3H, m, NH—CH—; N—CH$_2$—CH$_2$CH$_2$); 2.05–1.24 (6H, m, N—CH$_2$—CH$_2$CH$_2$).

EXAMPLE 33
(Method D):
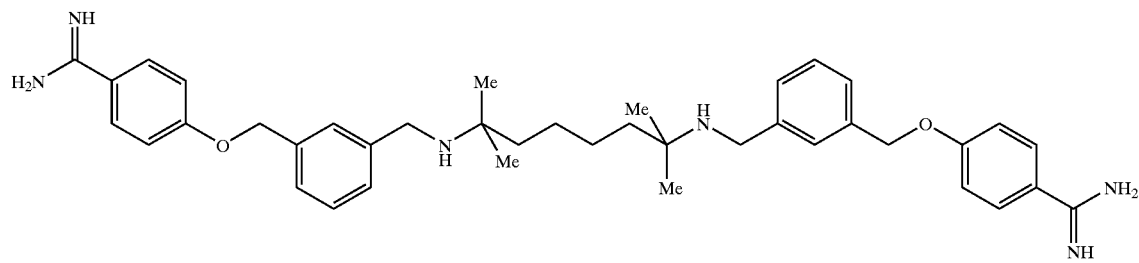
¹H-NMR(250 MHz, DMSO-d6):δ=9.61; 9.56; 9.38 (12H, 3, s, $NH_2$; $C(=NH_2^+)NH_2$); 8.22–7.43 (16H, m, aryl-H); 5.34 (4H, s, $OCH_2$—); 4.28 (4H, s, N—$CH_2$-phenyl); 2.05–1.27 (8H, m, C—$CH_2CH_2$—$CH_2CH_2$—C); 1.49 (12H, S, $CH_3$—C—$CH_3$).
EXAMPLE 34
(Method D):
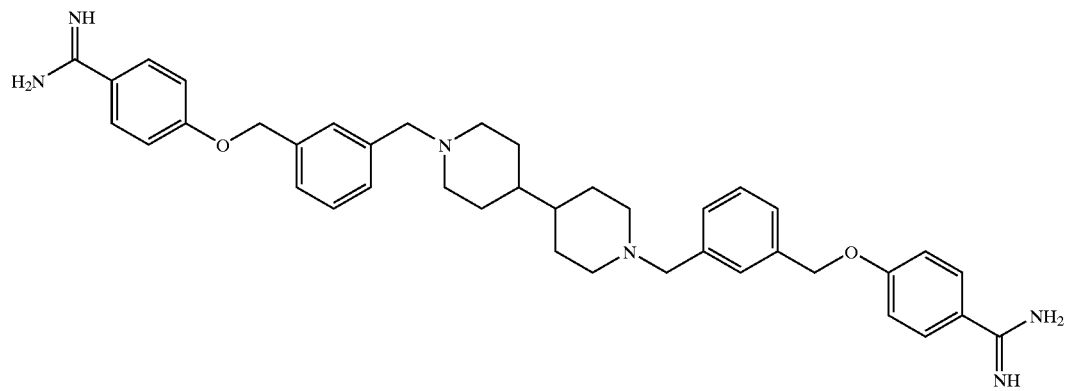
¹H-NMR(250 MHz, $CD_3OD$):δ=7.80–7.06 (16H, m, aryl-H); 5.18 (4H, s, $OCH_2$—); 3.48 (4H, s, N—$CH_2$-phenyl); 2.97–0.92 (18H, m, pip-H).
EXAMPLE 35
(Method E):
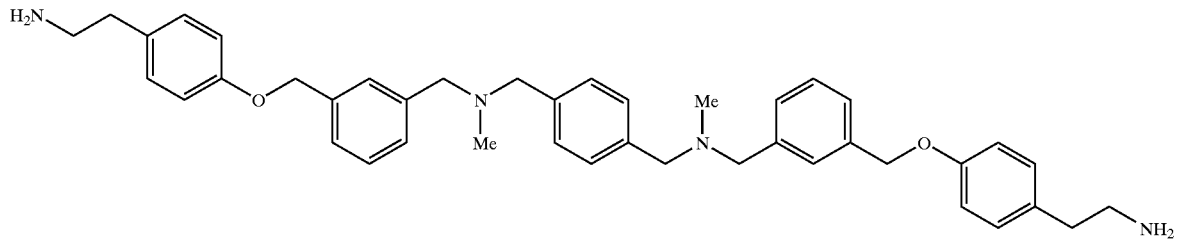
¹H-NMR(250 MHz, $CD_3OD$):δ=7.88–7.02 (2OH, m, aryl-H); 5.21 (4H, s, $OCH_2$—); 4.55; 4.43 (8H, 2s, N—$CH_2$-phenyl); 3.16; 2.93 (8H, 2m, N—$CH_2CH_2$-phenyl); 2.75 (6H, s, N—$CH_3$).

EXAMPLE 36
(Method B1):
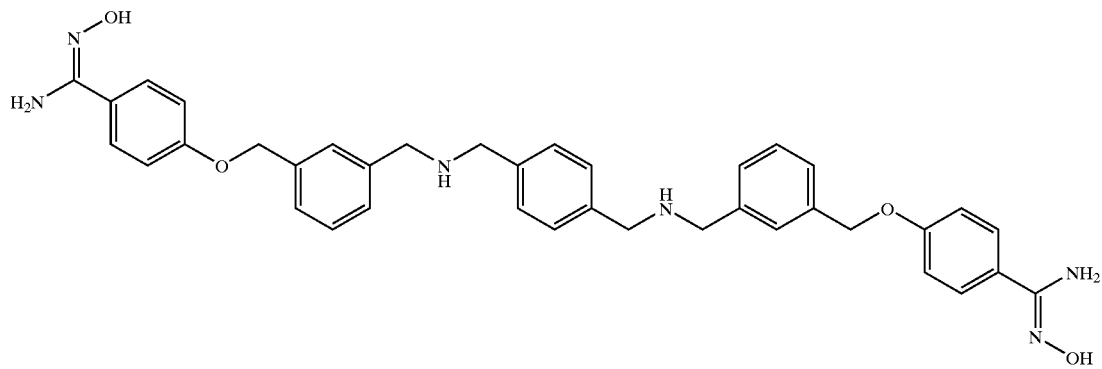
$^1$H-NMR(250 MHz, DMSO-d6):δ=13.16 (2H, s, C=N—OH); 11.33 (4H, s, NH$_2$); 10.26 (4H, s, NH$_2$); 7.86–7.22 (20H, m, aryl-H); 5.31 (4H, s, OCH$_2$—); 4.21 (8H, s, N—CH$_2$-phenyl).
EXAMPLE 37
(Method F):
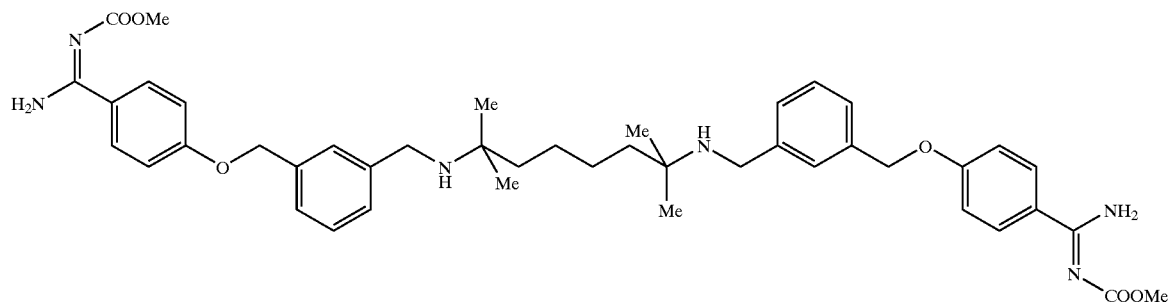
$^1$H-NMR(250 MHz, DMSO-d6):δ=9.14 (8H, s, NH$_2$); 8.11–7.04 (16H, m, aryl-H); 5.19 (4H, s, OCH$_2$—); 4.11 (4H, s, N—CH$_2$-phenyl); 3.59 (6H, s, OCH$_3$); 1.60–1.15 (8H, m, C—(CH$_2$)$_4$; 1.31 (18H, s, CH$_2$—C—CH$_3$).
EXAMPLE 38
(Method G):
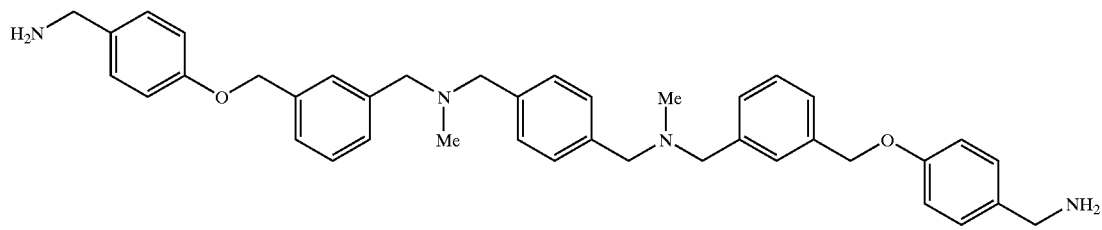
$^1$H-NMR(250 MHz, CD$_3$OD):δ=7.76–7.06 (20H, m, aryl-H); 5.19 (4H, s, OCH$_2$—); 4.51; 4.38 (8H, 2s, N—CH$_2$-phenyl); 4.05 (4H, s, CH$_2$—NH$_2$); 2.72 (6H, s, N—CH$_3$).

EXAMPLE 39
(Method D):
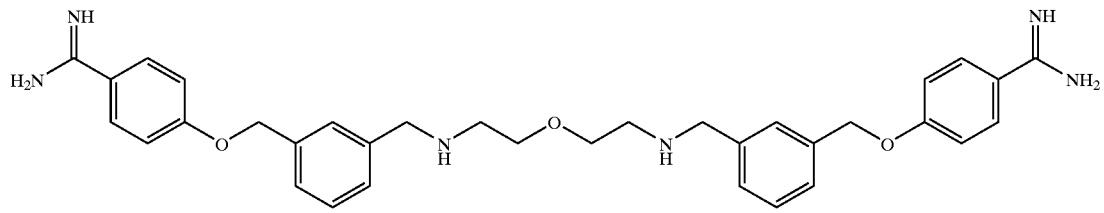
$^1$H-NMR(250 MHz, DMSO-d6):δ=9.80; 9.42; 9.19 (12H, 3s, $NH_2^+$, C(=$NH_2^+$)$NH_2$); 7.97–7.13 (16H, m, aryl-H); 5.22 (4H, s, $OCH_2$—); 4.20 (4H, s, N—$CH_2$-phenyl); 3.75; 3.06 (8H, 2m, N—$CH_2$—$CH_2$—O).
EXAMPLE 40
(Method D):
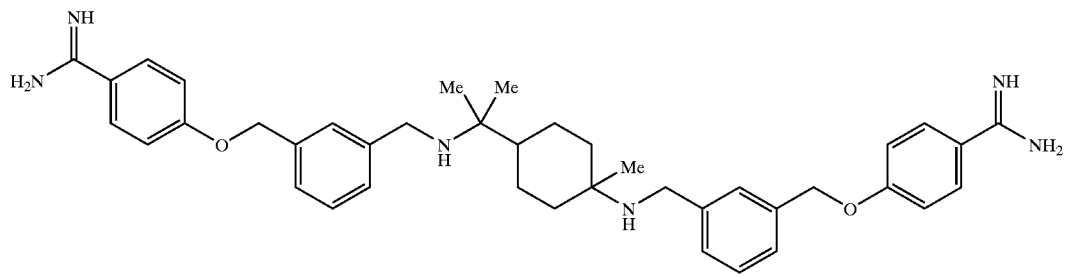
$^1$H-NMR(250 MHz, DMSO-d6):δ=9.31; 9.11; 9.09 (12H, 3s, $NH_2^+$, C(=$NH_2^+$)$NH_2$); 8.00–7.15 (16H, m, aryl-H); 5.23 (4H, s, $OCH_2$); 4.11 (4H, s, N—$CH_2$-phenyl); 2.37–0.83 (9H, m, pip-H); 1.38 (6H, s, C($CH_3$)$_2$); 1.29 (3H, s, C—$CH_3$).
EXAMPLE 41
(Method D):
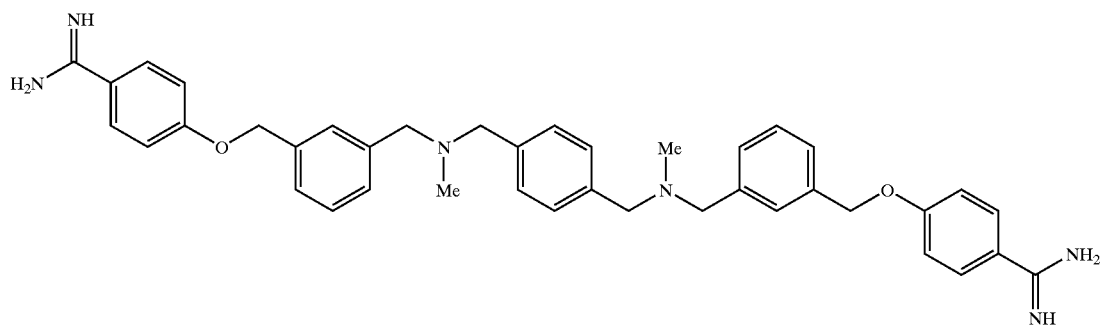
$^1$H-NMR(250 MHz, $CD_3OD$):δ=7.80–7.06 (16H, m, aryl-H); 5.18 (4H, s, $OCH_2$—); 3.48 (4H, s, N—$CH_2$-phenyl); 2.97–0.92 (18H, m, pip-H).

EXAMPLE 42
(Method E):
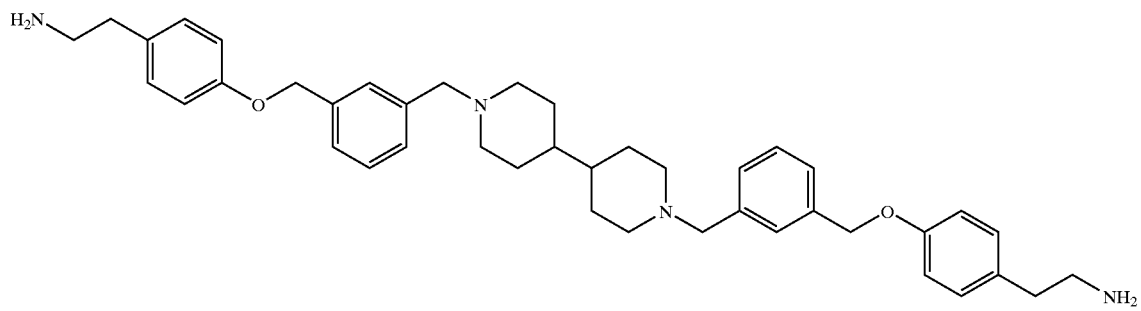
$^1$H-NMR(250 MHz, CD$_3$OD):δ=7.43–6.85 (16H, m, aryl-H); 5.15 (4H, s, OCH$_2$); 3.49 (4H, s, N—CH$_2$-phenyl); 2.88–0.93 (26H, m, CH$_2$—CH$_2$—NH$_2$; pip.-H).
EXAMPLE 43
(Method D):
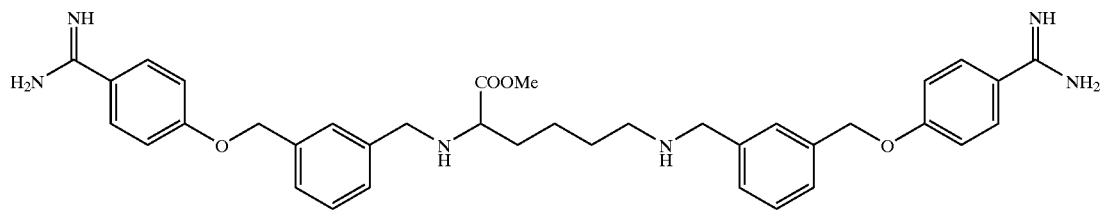
EXAMPLE 44
(Method D):
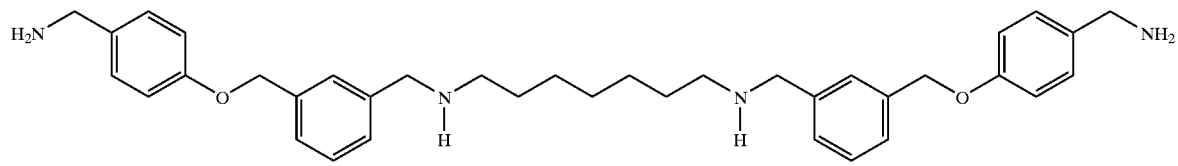
EXAMPLE 45
(Method D):
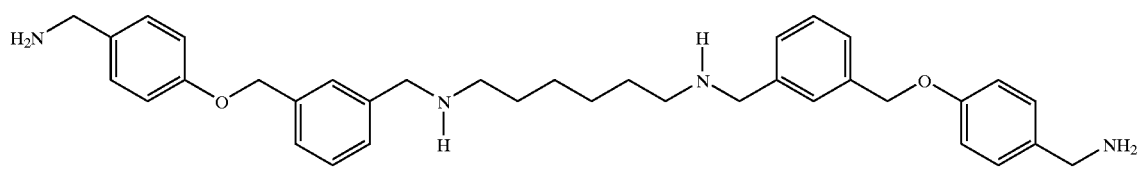

EXAMPLE 46
(Method E):
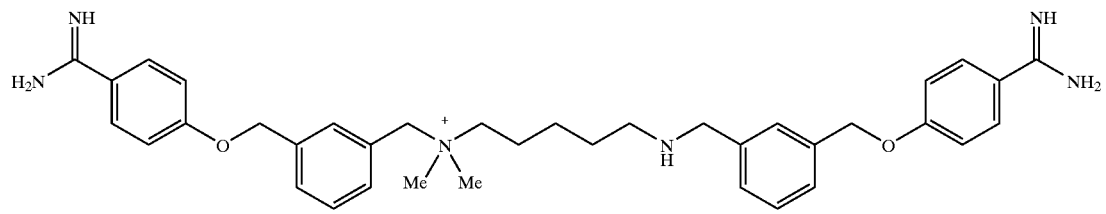
EXAMPLE 47
(Method D):
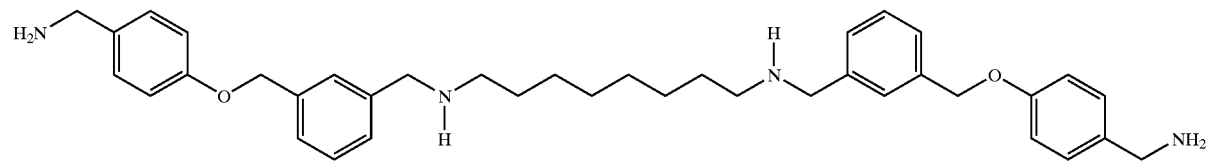
EXAMPLE 48
(Method D):
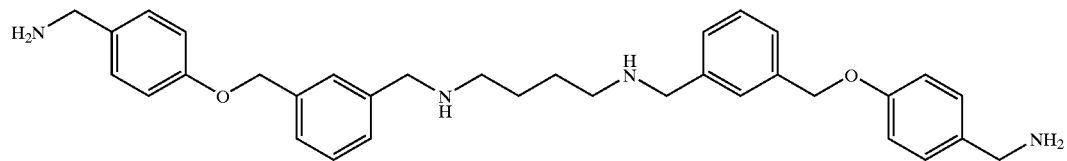
EXAMPLE 49
(Method D):
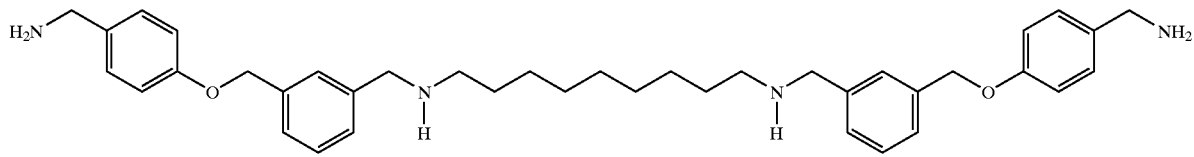
EXAMPLE 50
(Method D):
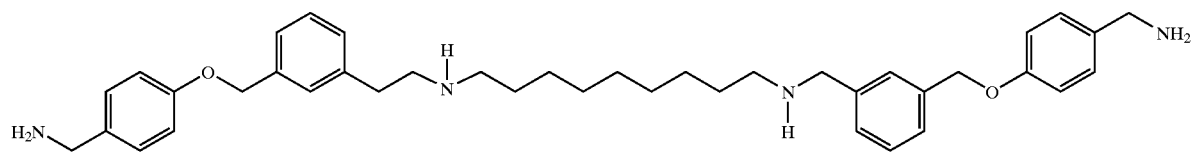

EXAMPLE 51
(Method D):
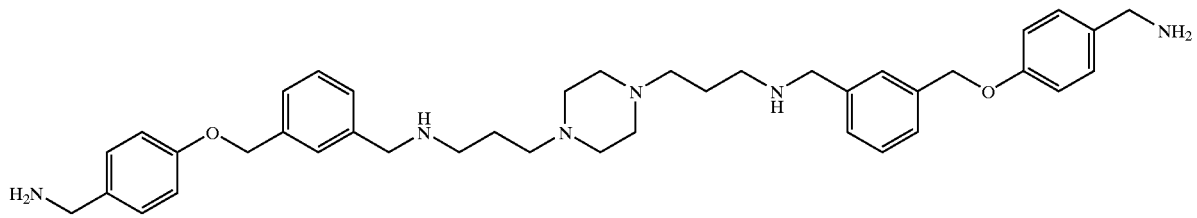
EXAMPLE 52
(Method D):
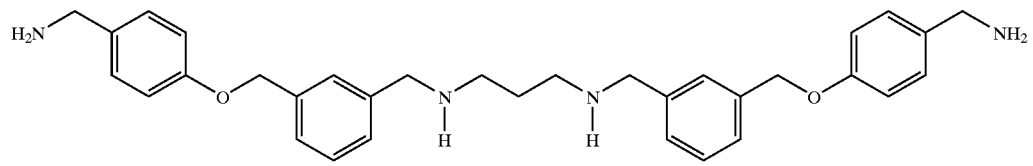
EXAMPLE 53
(Method B1):
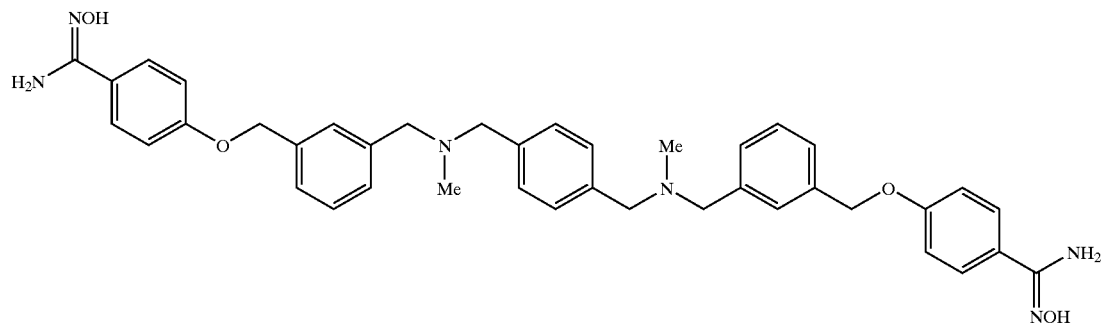
EXAMPLE 54
(Method G):
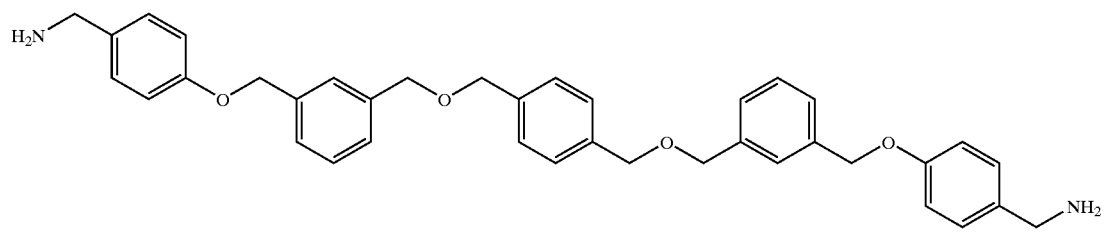

EXAMPLE 55
(Method F):
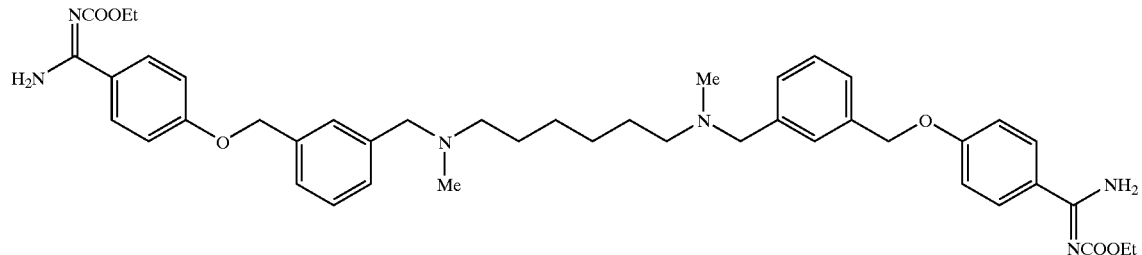
EXAMPLE 56
(Method B1/B2):
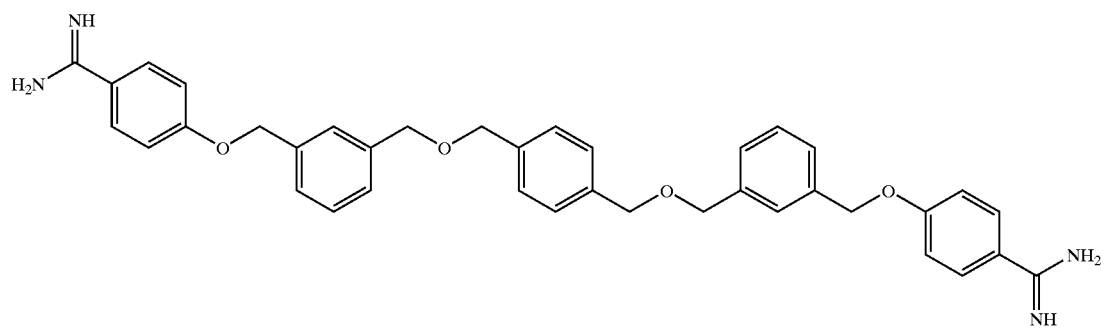
EXAMPLE 57
(Method F):
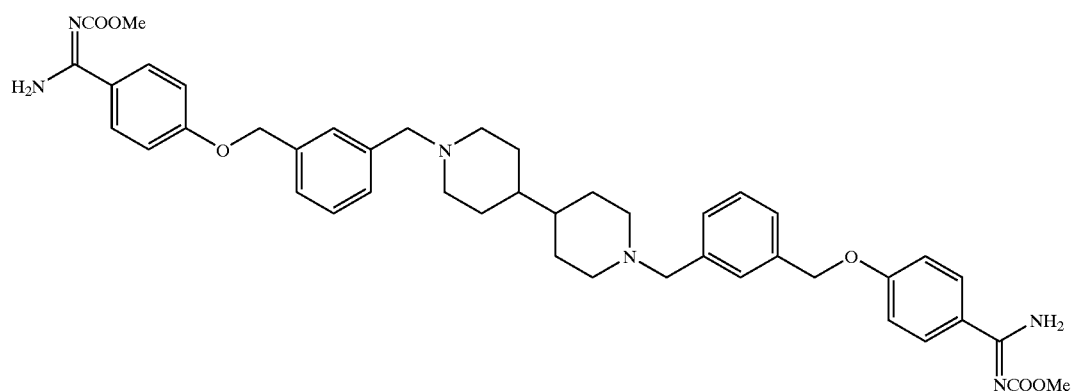

EXAMPLE 58
(Method F):
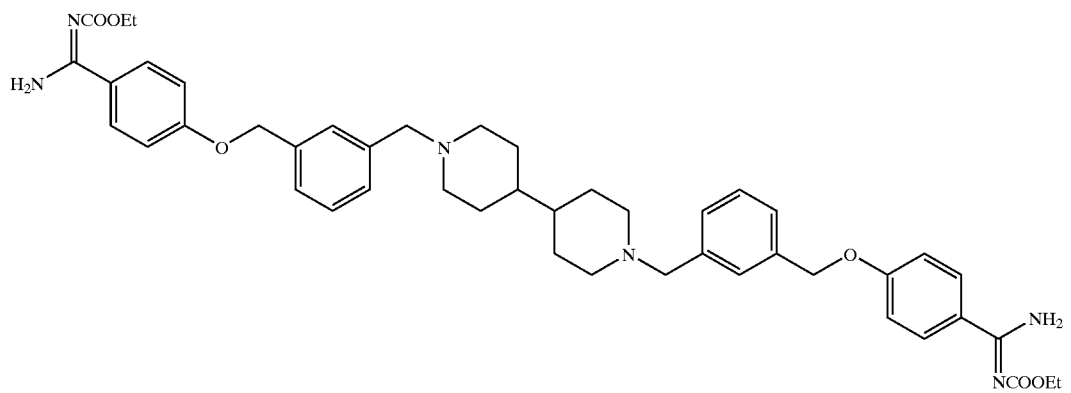
EXAMPLE 59
(Method F):
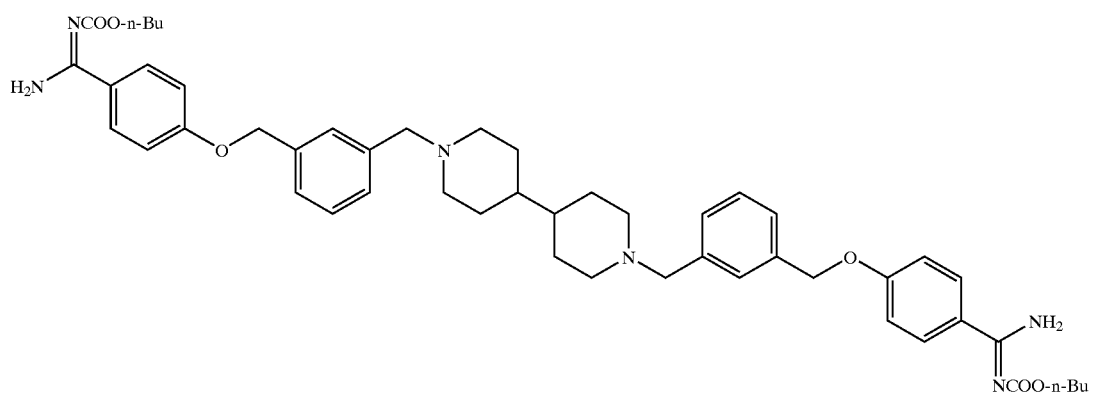
EXAMPLE 60
(Method F):
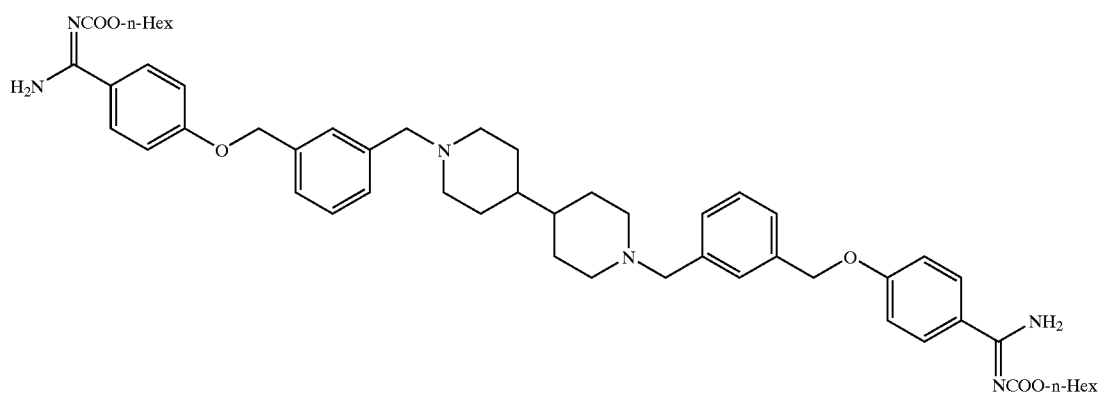

EXAMPLE 61
(Method F):
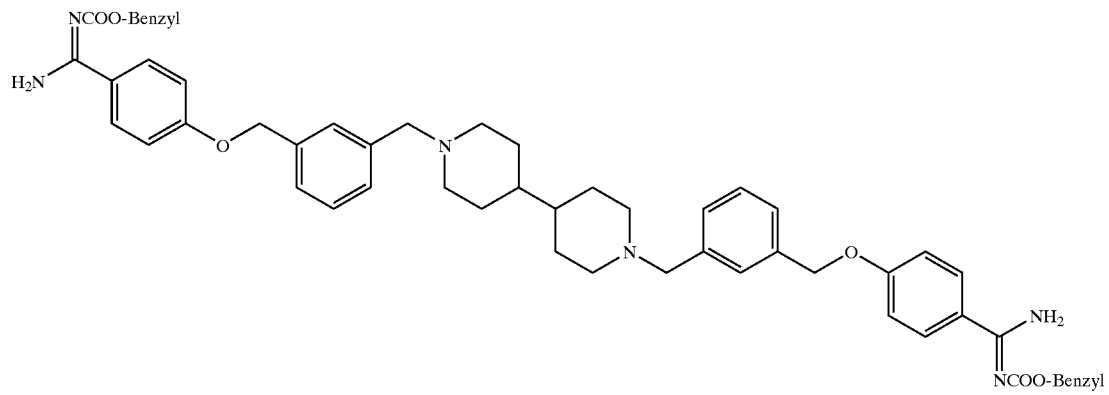
EXAMPLE 62
(Method D):
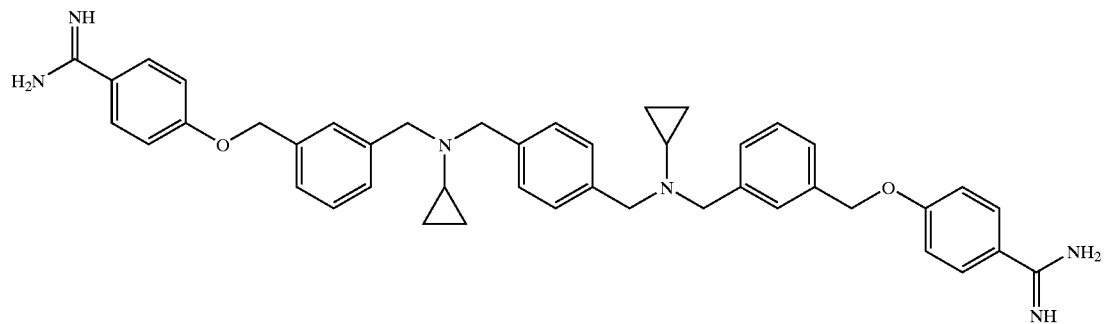
EXAMPLE 63
(Method D):
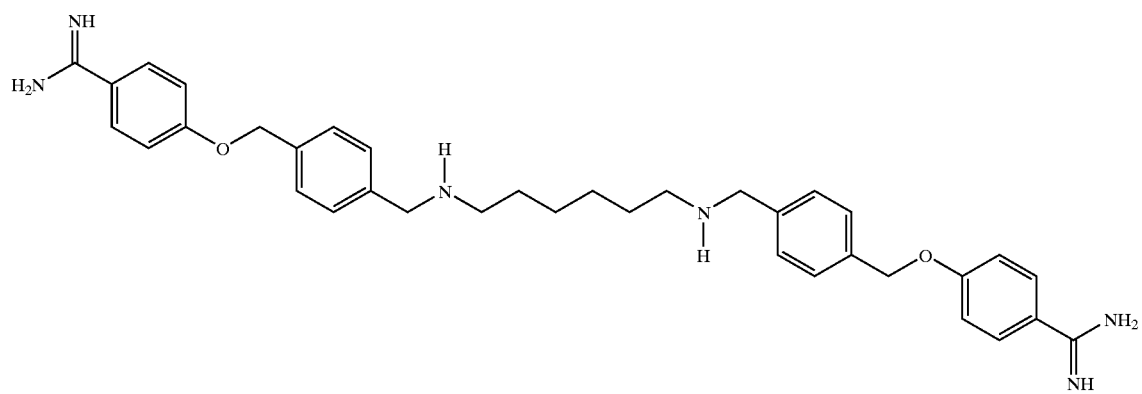

EXAMPLE 64
(Method D):
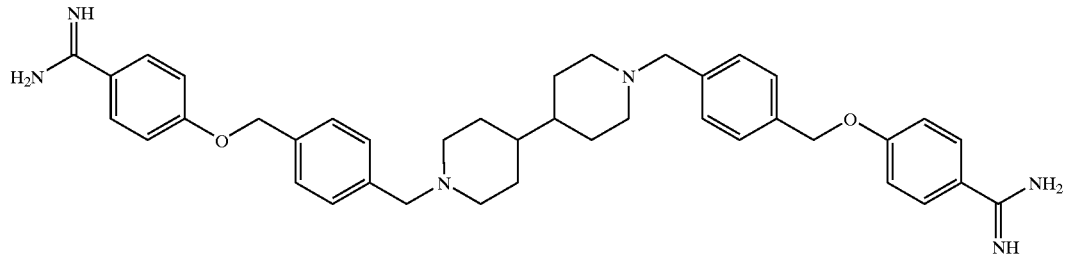
EXAMPLE 65
(Method D):
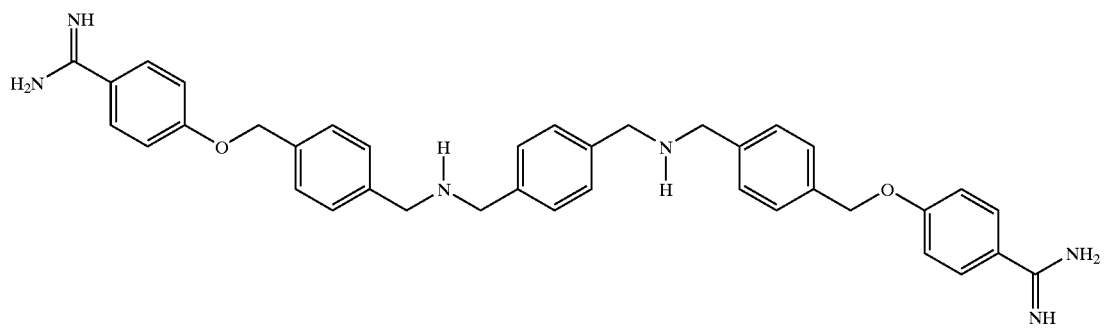
EXAMPLE 66
(Method B1):
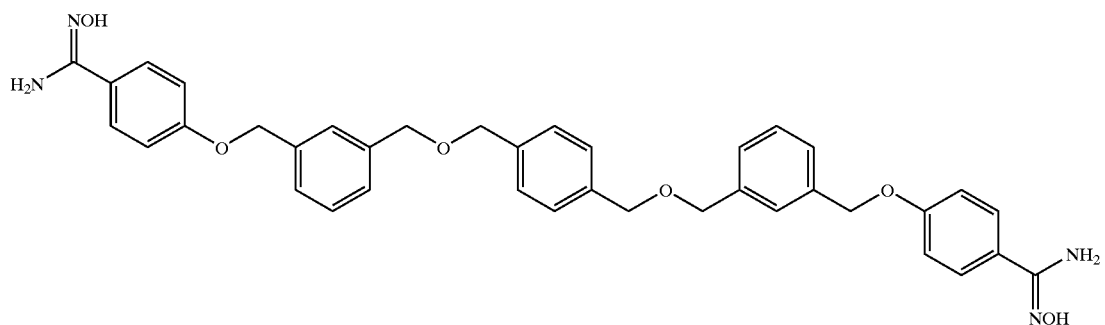

EXAMPLE 67

(Method B1):

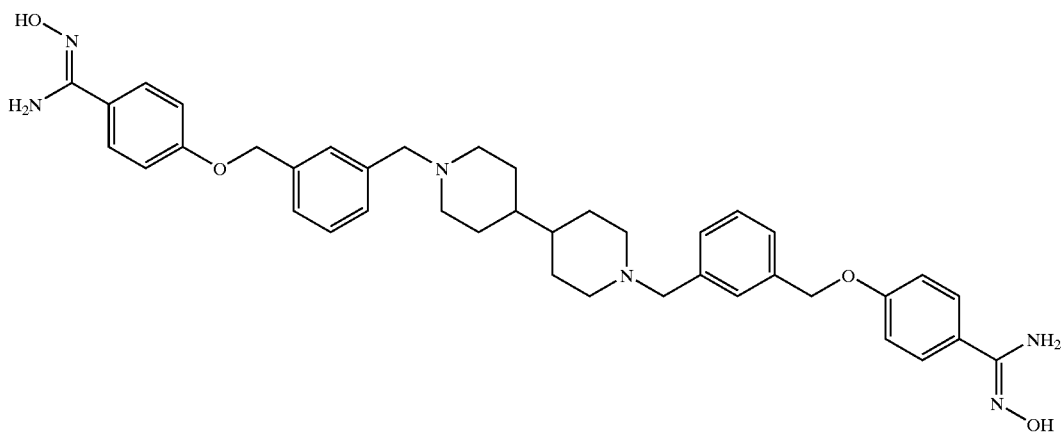

EXAMPLE 68

(Method G):

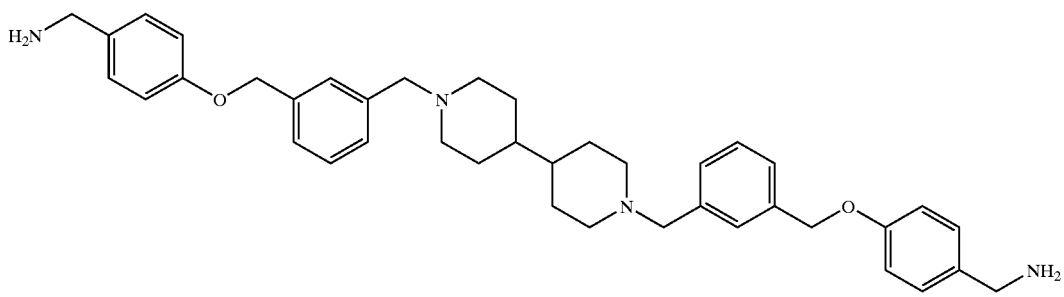

The compounds according to the invention are characterised by their tryptase-inhibiting activity. This ability to inhibit tryptase was investigated using the test described below.

The measurement is carried out in Tris HCl buffer (100 mM), which additionally contains calcium (5 mM) and heparin (100 mg/ml), at pH 7.4. The standard used is rh beta tryptase which may be obtained commercially from Promega, for example. The substrate used is N-p-tosyl—Gly-Pro-Lys-para-nitroaniline in a concentration of 0.6 mM. The substrate is digested with tryptase to form p-nitroaniline which can be measured at 405 nm. Usually, an incubation period of 5 minutes and an incubation temperature of 37° C. are chosen. The enzyme activity used is 0.91 U/ml. The measurements are carried out in an Autoanalyser (Cobas Bio) made by Hofmann LaRoche. The potential inhibitory substances are used in concentrations of 10 $\mu$M in the screening, the inhibition of the tryptase being given in percent. The $IC_{50}$ (concentration at which 50% of the enzyme activity is inhibited) is determined at over 70% inhibition. After 5 minutes' pre-incubation of the potential inhibitory substances, the substrate is added to start the reaction, the formation of p-nitroaniline being taken as a measurement of the enzyme activity after 5 minutes, after testing the linearity.

The IC50 values obtained for the compounds according to the invention are shown in Table 1.

TABLE 1

| Example | salt form | $IC_{50}$ value [nM] |
|---|---|---|
| 2 | diacetate | 19 |
| 7 | tetrachloride | 4.3 |
| 10 | tetrachloride | 35 |
| 11 | tetrachloride | 4 |
| 14 | tetrachloride | 13 |
| 15 | tetrachloride | 23 |
| 16 | tetrachloride | 12 |
| 17 | tetrachloride | 1.4 |
| 18 | tetrachloride | 10.7 |
| 19 | tetrachloride | 10 |
| 20 | tetrachloride | 7.1 |
| 22 | tetrachloride | 27.4 |
| 23 | tetrachloride | 1.1 |
| 24 | tetrachloride | 3.1 |
| 25 | tetrachloride | 1.2 |
| 26 | tetrachloride | 0.8 |
| 27 | tetrachloride | 1.7 |
| 28 | tetrachloride | 5.3 |
| 29 | tetrachloride | 1.7 |
| 30 | tetrachloride | 6.8 |
| 31 | tetrachloride | 13 |
| 32 | tetrachloride | 32.4 |
| 33 | tetrachloride | 2.5 |
| 34 | tetrachloride | 0.8 |
| 35 | tetrachloride | 31.6 |
| 39 | tetrachloride | 12 |
| 40 | tetrachloride | 5 |
| 41 | tetrachloride | 4.6 |

TABLE 1-continued

| Example | salt form | $IC_{50}$ value [nM] |
|---|---|---|
| 42 | tetrachloride | 30.9 |
| 56 | diacetate | 19 |
| 62 | tetrachloride | 41 |
| 63 | tetrachloride | 0.74 |
| 64 | tetrachloride | 1.1 |
| 65 | tetrachloride | 0.59 |
| 68 | tetrachloride | 2.5 |

The trytase inhibitors according to the invention may be administred orally, transdermally, by inhalation or parenterally. The compounds according to the invention occur as active ingredients in conventional preparations, for example in compositions which consist essentially of an inert pharmaceutical carrier and an effective dose of the active substance, such as for example tablets, coated tablets, capsules, powders, solutions, suspensions, emulsions, syrups, suppositories, transdermal systems, etc. An effective dose of the compounds according to the invention is between 1 and 100, preferably between 1 and 50, most preferably between 5–30 mg/dose for oral administration, and between 0.001 and 50, preferably between 0.1 and 10 mg/dose for intravenous or intramuscular administration. For inhalation, according to the invention, solutions containing 0.01 to 1.0, preferably 0.1 to 0.5% active substance are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 800 mg, preferably 10–300 mg per adult.

The Examples which follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed. It is cooled to 38° C. and poured into slightly chilled suppository moulds.

What is claimed is:

1. A compound of formula (I)

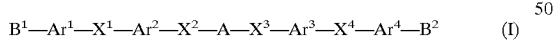

wherein:

$B^1$ and $B^2$, which are identical or different, are each —C(=NR$^1$)—NR$^{1'}$H, —CH$_2$NH$_2$, —CH$_2$CH$_2$NH$_2$, or —NH—C(=NH)—NH$_2$;

$R^1$ and $R^{1'}$, which are identical or different, are each hydrogen, OH, —COR$^2$, or —COOR$^2$;

$R^2$ is hydrogen, $C_1$–$C_{18}$-alkyl, Ar$^5$, or Ar$^5$—$C_1$–$C_6$-alkyl;

Ar$^1$, Ar$^2$, Ar$^3$, and Ar$^4$, which are identical or different, are each $C_6$–$C_{10}$-aryl- which is optionally mono- to tetrasubstituted by one or more groups selected from $C_3$–$C_{10}$-cycloalkyl, F, Cl, Br, I, OH, OR$^3$, SR$^3$, NR$^3$R$^4$, COOR$^3$, $C_1$–$C_6$-alkyl, $C_2$–$C_6$-alkenyl $C_2$–$C_6$-alkynyl, wherein in the substituents $C_1$–$C_6$-alkyl and $C_2$–$C_6$-alkenyl, one or more hydrogen atoms are optionally replaced by F or OR$^3$;

Ar$^5$ is $C_6$–$C_{10}$-aryl- which is optionally mono- to tetrasubstituted by one or more groups selected from $C_3$–$C_{10}$-cycloalkyl, F, Cl, Br, I, OH, OR$^3$, SR$^3$, NR$^3$R$^4$, COR$^3$, $C_1$–$C_6$-alkyl, $C_2$–$C_6$-alkenyl, and $C_2$–$C_6$-alkynyl, wherein in the substituents $C_1$–$C_6$-alkyl and $C_2$–$C_6$-alkenyl, one or more hydrogen atoms are optionally replaced by F or OR$^3$, or a 5–10-membered mono- or bicyclic heteroaryl ring, wherein up to three carbon atoms are replaced by one or more heteroatoms selected from oxygen, nitrogen, and sulfur and which are optionally mono- to tetrasubstituted by one or more groups selected from $C_1$–$C_{10}$-cycloalkyl, F, Cl, Br, I, OH, OR$^3$, SR$^3$, NR$^3$R$^4$, COOR$^3$, $C_1$–$C_6$-alkyl, $C_2$–$C_6$-alkenyl, and $C_2$–$C_6$-alkynyl, wherein in the substituents $C_1$–$C_6$-alkyl and $C_2$–$C_6$-alkenyl, one or more hydrogen atoms are optionally replaced by F or OR$^3$;

$R^3$ and $R^4$, which are identical or different, are each hydrogen or a group selected from $C_1$–$C_6$-alkyl and $C_3$–$C_6$-cycloalkyl, wherein one or more hydrogen atoms are optionally replaced by F;

$X^1$ and $X^4$, which are identical or different, are each —(CH$_2$)$_n$O— or —(CH$_2$)$_n$—S—;

$X^2$ and $X^3$, which are identical or different, are each —(CH$_2$)$_n$—;

n is 1 or 2 in each case;

A is —E$^1$—(CH$_2$)$_r$—E$^2$—, wherein r is 0, 1, 2, 3, 4, 5, or 6, and E$^1$ and E$^2$ are each piperidine or piperazine, or a tautomer or pharmaceutically acceptable salt thereof.

2. The compound of formula (I) according to claim 1, wherein:

$R^2$ is hydrogen, $C_1$–$C_{14}$-alkyl, Ar$^5$, or Ar$^5$—$C_1$–$C_6$-alkyl;

Ar$^1$, Ar$^2$, Ar$^3$, and Ar$^4$, which are identical or different, are each $C_6$–$C_{10}$-aryl- which are optionally mono- to tetrasubstituted by one or more groups selected from $C_3$–$C_8$-cycloalkyl, F, Cl, Br, I, OH, OR$^3$, NR$^3$R$^4$, COOR$_3$, $C_1$–$C_6$-alkyl, $C_2$–$C_6$-alkenyl, and $C_2$–$C_6$-alkynyl, wherein in the substituents $C_1$–$C_6$-alkyl and $C_2$–$C_6$-alkenyl, one or more hydrogen atoms are optionally replaced by F; and Ar$^5$ is $C_6$–$C_{10}$-aryl- which is optionally mono- to tetrasubstituted by one or more groups selected from $C_3$–$C_8$-cycloalkyl, F, Cl, Br, I, OH, OR$^3$, NR$^3$R$^4$, COOR$_3$, $C_1$–$C_6$-alkyl, $C_2$–$C_6$-alkenyl, and $C_2$–$C_6$-alkynyl, wherein in the substituents $C_1$–$C_6$-alkyl and $C_2$–$C_6$-alkenyl, one or more hydrogen atoms are optionally replaced by F, or a 5–10-membered mono- or bicyclic heteroaryl ring, wherein up to three carbon atoms are replaced by one or more heteroatoms selected from oxygen, nitrogen, and sulfur and which are optionally mono- to tetrasubstituted by one or more groups selected from F, OR$^3$, COOR$^3$, or $C_1$–$C_6$-alkyl, wherein in the substituent $C_1$–$C_6$-alkyl, one or more hydrogen atoms are optionally replaced by F, or a tautomer or pharmaceutically acceptable salt thereof.

3. The compound of formula (I) according to claim 1, wherein:

$R^2$ is hydrogen, $C_1$–$C_{10}$-alkyl, or Ar$^5$—$C_1$–$C_4$-alkyl;

Ar$^1$, Ar$^2$, Ar$^3$, Ar$^4$, and Ar$^5$, which are identical or different, are each phenyl or naphthyl which are optionally mono-, di-, or trisubstituted by one or more groups selected from F, OR$^3$, NR$^3$R$^4$, COOR$_3$, or $C_1$–$C_6$-alkyl, wherein in the substituent $C_1$–$C_6$-alkyl, one or more hydrogen atoms are optionally replaced by F or OR$^3$;

R³ and R⁴, which are identical or different, are each hydrogen or a group selected from cyclopropyl, cyclopentyl, cyclohexyl, and $C_1$–$C_4$-alkyl, wherein one or more hydrogen atoms are optionally replaced by F; and r is 0, 1, 2, 3, or 4, or a tautomer or pharmaceutically acceptable salt thereof.

4. The compound of formula (I) according to claim 1, wherein:

R² is hydrogen, $C_1$–$C_6$-alkyl, or benzyl;

Ar¹, Ar², Ar³, and Ar⁴, which are identical or different, are each phenyl which are optionally mono-, di-, or trisubstituted by one or more groups selected from F, OR³, NR³R⁴, COOR₃, or $C_1$–$C_4$-alkyl, wherein in the substituent $C_1$–$C_4$-alkyl, one or more hydrogen atoms are optionally replaced by F;

R³ and R⁴, which are identical or different, are each hydrogen or a group selected from cyclopropyl, cyclopentyl, cyclohexyl, and $C_1$–$C_4$-alkyl, wherein one or more hydrogen atoms are optionally replaced by F; and r is 0, 1, 2, or 3, or a tautomer or pharmaceutically acceptable salt thereof.

5. The compound of formula (I) according to claim 1, wherein:

B¹ and B², which are identical or different, are each —C(=NR¹)—NH₂, —CH₂NH₂, or —CH₂CH₂NH₂;

R² is hydrogen, methyl, ethyl, propyl, butyl, pentyl, hexyl, or benzyl;

Ar¹, Ar², Ar³, and Ar⁴ are each phenyl;

n is 1; and r is 0, 1,2 or 3, or a tautomer or pharmaceutically acceptable salt thereof.

6. The compound of formula (I) according to claim 1, wherein n is 1.

7. The compound of formula (I) according to claim 1, wherein:

X¹ is —O—(CH₂)—; and

X⁴ is —(CH₂)—O—.

8. A compound of formula (IA)

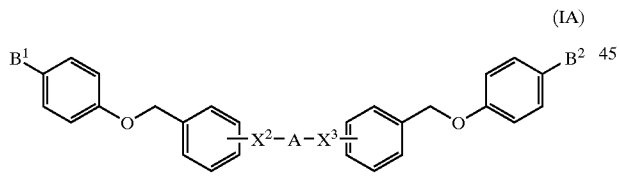

(IA)

wherein:

B¹ and B², which are identical or different, are each —C(=NR¹)—NR¹'H, —CH₂NH₂, —CH₂CH₂NH₂, or —NH—C(=NH)—NH₂;

R¹ and R¹', which are identical or different, are each hydrogen, OH, —COR², or —COOR²;

R² is hydrogen, $C_1$–$C_{18}$-alkyl, aryl, or aryl-$C_1$–$C_6$-alkyl;

X² and X³, which are identical or different, are each —(CH₂)ₙ—, where n is 1 or 2; and A is —E¹—(CH₂)ᵣ—E²—, wherein r is 0, 1, 2, 3, 4, 5, or 6, and E¹ and E² are each piperidine or piperazine, or a tautomer or pharmaceutically acceptable salt thereof.

9. The compound of the formula (IA) according to claim 8, wherein R² is hydrogen, $C_1$–$C_{14}$-alkyl, aryl, or aryl-$C_1$–$C_6$-alkyl, or a tautomer or pharmaceutically acceptable salt thereof.

10. The compound of formula (IA) according to claim 9, wherein R² is hydrogen, $C_1$–$C_{10}$-alkyl, or aryl-$C_1$–$C_6$-alkyl, or a tautomer or pharmaceutically acceptable salt thereof.

11. The compound of formula (IA) according to claim 8, wherein R² is hydrogen, $C_1$–$C_6$-alkyl, or benzyl, or a tautomer or pharmaceutically acceptable salt thereof.

12. The compound of formula (IA) according to claim 8, wherein:

B¹ and B², which are identical or different, are each —C(=NR¹)—NH₂, —CH₂NH₂, or —CH₂CH₂NH₂;

R² is hydrogen, methyl, ethyl, propyl, butyl, pentyl, hexyl, or benzyl; and n is 1, or a tautomer or pharmaceutically acceptable salt thereof.

13. The compound of formula (I) according to claim 1, wherein:

the grouping B¹—Ar¹—X¹—Ar²—X²— is a group selected from:

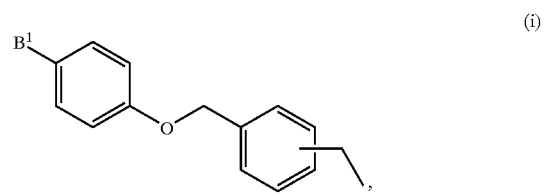

(i)

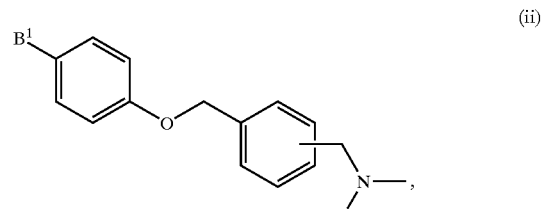

(ii)

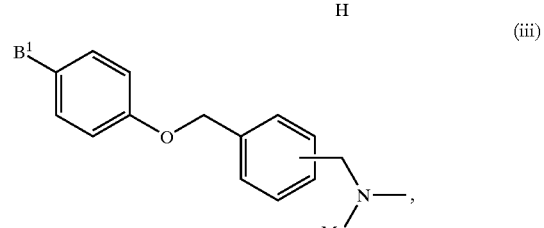

(iii)

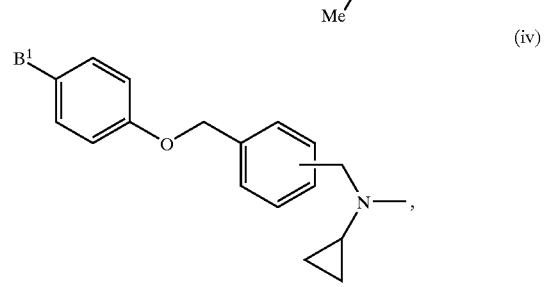

(iv)

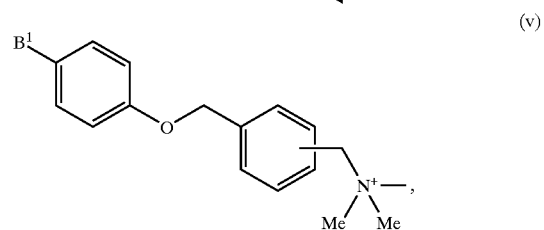

(v)

(vi)
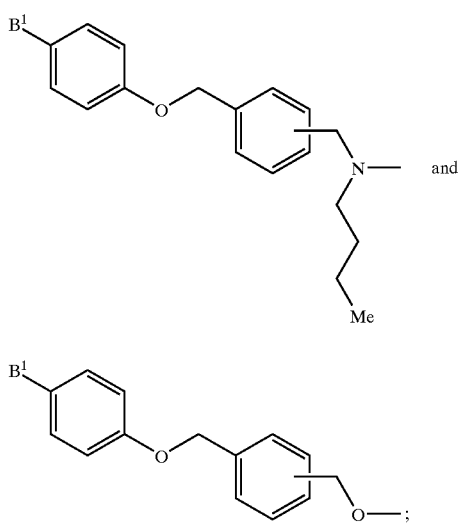
(vii)

the grouping —X³—Ar³—X⁴—Ar⁴—B² is a group selected from:

(i')
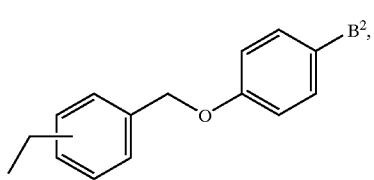

(ii')
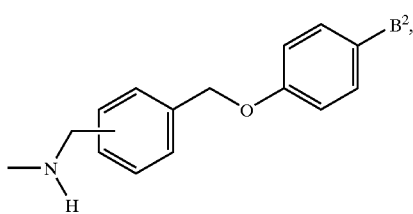

(iii')
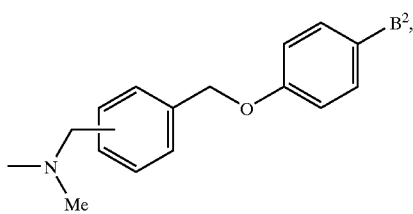

(iv')
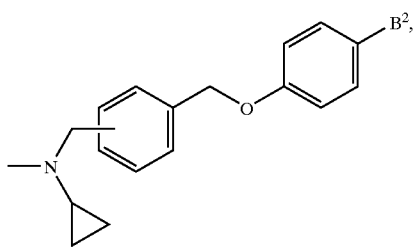

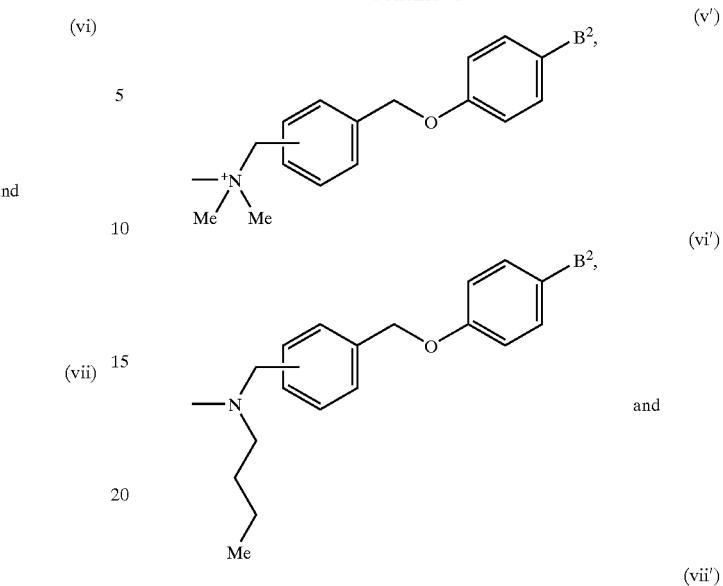
(v')
(vi')
and
(vii')

wherein:
B¹ and B², which are identical or different, are each —C(=NR¹)—NR¹'H, —CH₂NH₂, —CH₂CH₂NH₂, or —NH—C(=NH)—NH₂;
R¹ and R¹', which are identical or different, are each hydrogen or OH;

A is 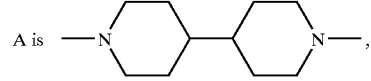, or a tautomer or pharmaceutically acceptable salt thereof.

14. A compound of formula (I) according to claim 1, wherein:
the grouping B¹—Ar¹—X¹—Ar²—X²— is a group selected from:

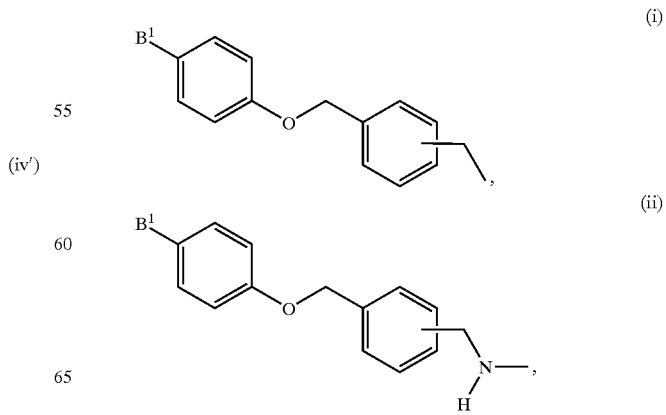
(i)
(ii)

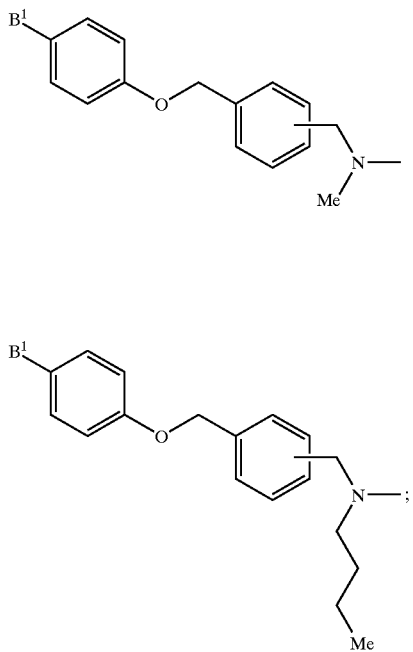

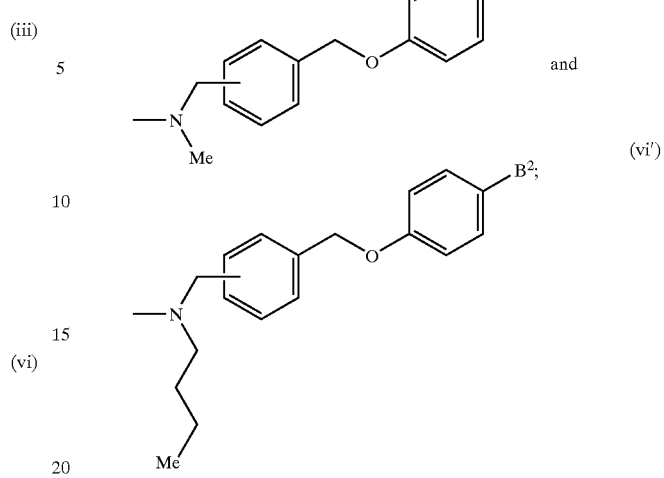

the grouping —X³—Ar³—X⁴—Ar⁴—B² is a group selected from:

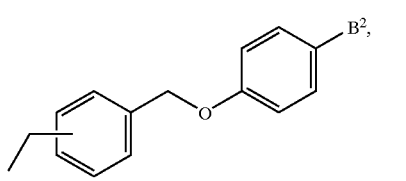

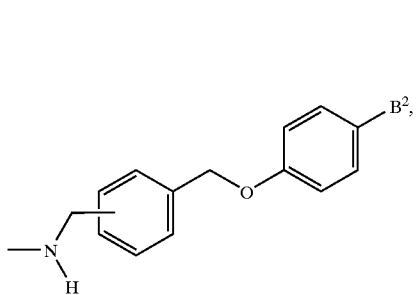

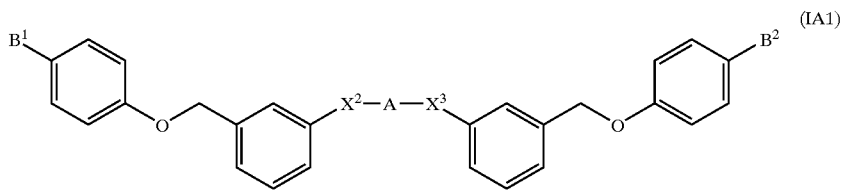

wherein
B¹ and B², which are identical or different, are each —C(=NR¹)—NR¹'H or —CH$_2$NH$_2$,
R¹ and R¹', which are identical or different, are each hydrogen or OH, A is a 4,4'-bipiperidine linker, or a tautomer or pharmaceutically acceptable salt thereof.

15. A compound of formula (IA1)

(IA1)

wherein:
B¹ and B², which are identical or different, are each —C(=NR¹)—NR¹'H, —CH$_2$NH$_2$, —CH$_2$CH$_2$NH$_2$, or —NH—C(=NH)—NH$_2$;
R¹ and R¹', which are identical or different, are each hydrogen, OH, —COR², or —COOR²;
R² is hydrogen, C$_1$–C$_{18}$-alkyl, aryl, or aryl-C$_1$–C$_6$-alkyl;
X² and X³, which are identical or different, are each —(CH$_2$)$_n$—, where n is 1 or 2; and
A is —E¹—(CH$_2$)$_r$—E²—, wherein r is 0, 1, 2, 3, 4, 5, or 6, and E¹ and E² are each piperidine or piperazine,
or a tautomer or pharmaceutically acceptable salt thereof.

16. The compound of formula (IA1) according to claim 15, wherein R² is hydrogen, C$_1$–C$_{14}$-alkyl, aryl, or aryl-C$_1$–C$_6$-alkyl, or a tautomer or pharmaceutically acceptable salt thereof.

17. A compound of formula (IA1) according to claim 15, wherein:
R² is hydrogen, C$_1$–C$_{10}$-alkyl, or aryl-C$_1$–C$_4$-alkyl; and
r is 0, 1, 2, 3, or 4,
or a tautomer or pharmaceutically acceptable salt thereof.

18. The compound of formula (IA1) according to claim 15, wherein:

R² is hydrogen, C₁–C₆-alkyl, or benzyl; and r is 0, 1, 2, or 3, or a tautomer or pharmaceutically acceptable salt thereof.

19. The compound of formula (IA1) according to claim 15, wherein:

B¹ and B², which are identical or different, are each —C(=NR¹)—NH₂, —CH₂NH₂, or —CH₂CH₂NH₂;

R² is hydrogen, methyl, ethyl, propyl, butyl, pentyl, hexyl, or benzyl;

n is 1; and r is 0, 1, 2, or 3, or a tautomer or pharmaceutically acceptable salt thereof.

20. A compound of formula (I) according to claim 1, wherein A is

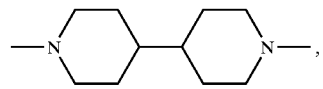

or a tautomer or pharmaceutically acceptable salt thereof.

21. The compound of formula (I) according to claim 1, wherein —X²—A—X³- is

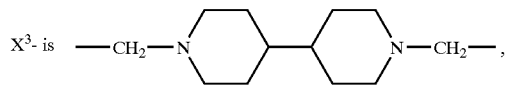

or a tautomer or pharmaceutically acceptable salt thereof.

22. A compound selected from the group consisting of:

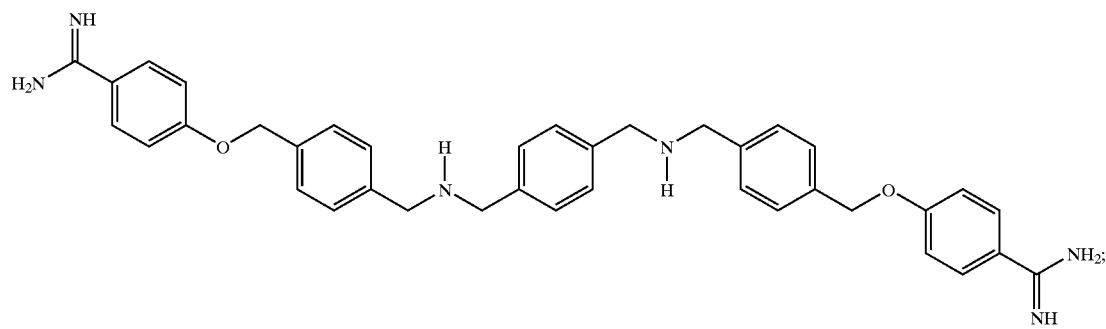

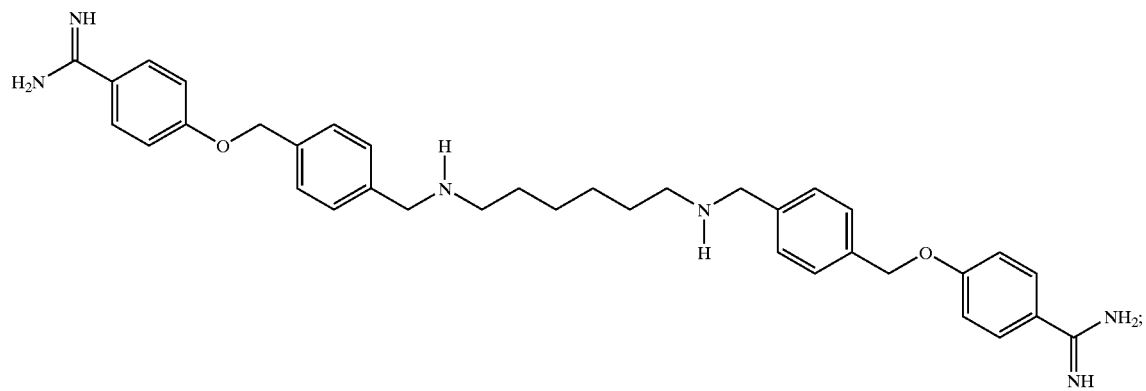

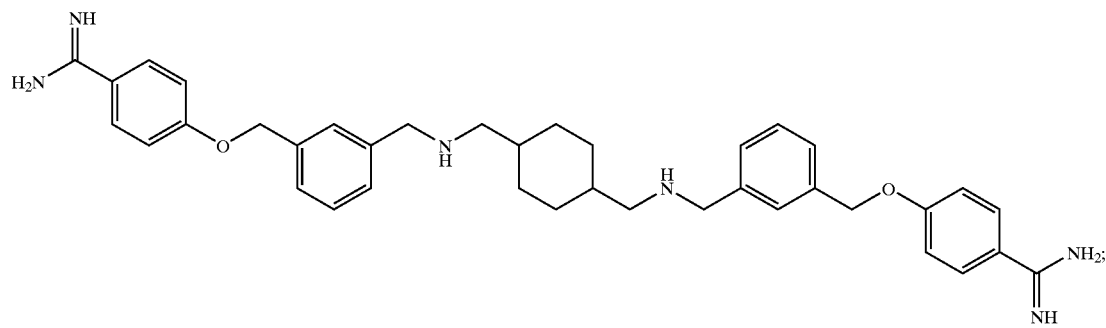

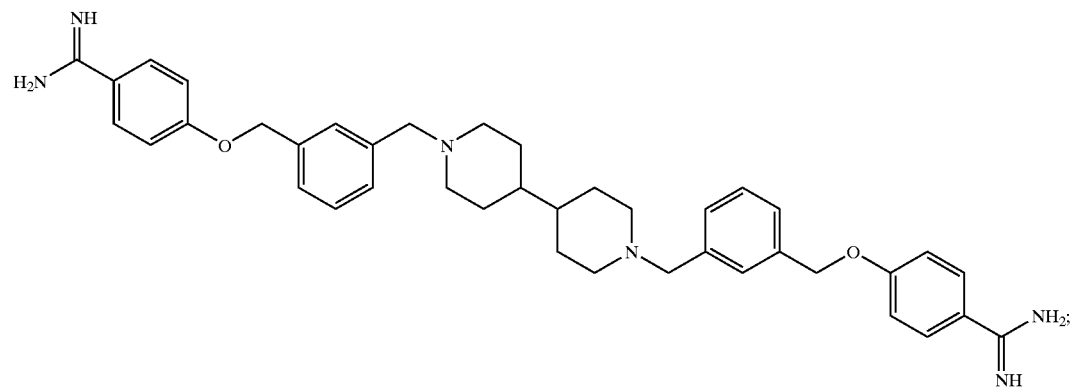
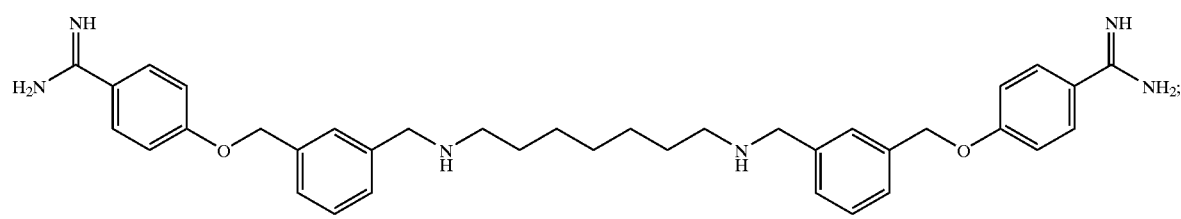
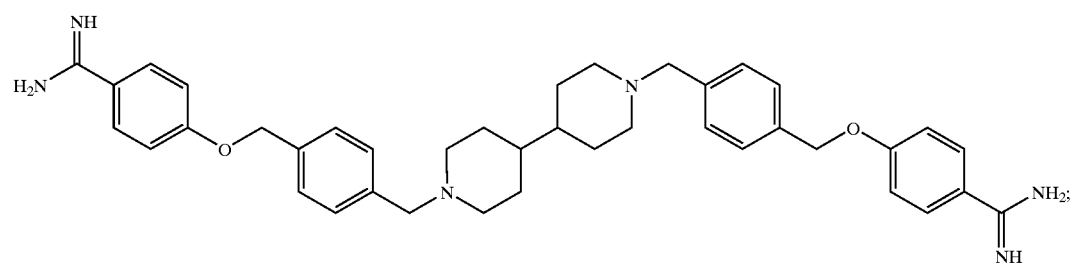
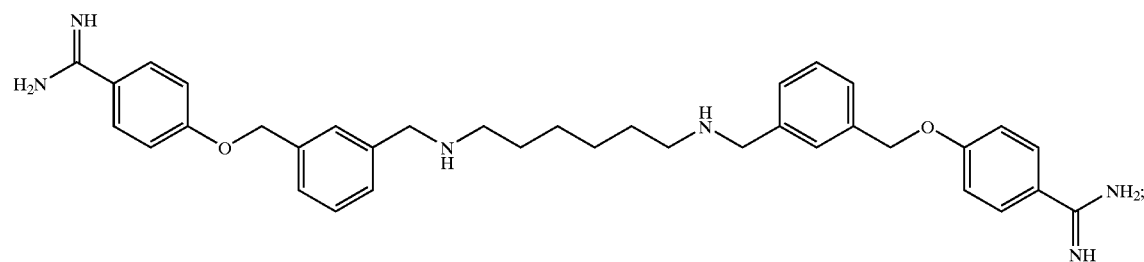
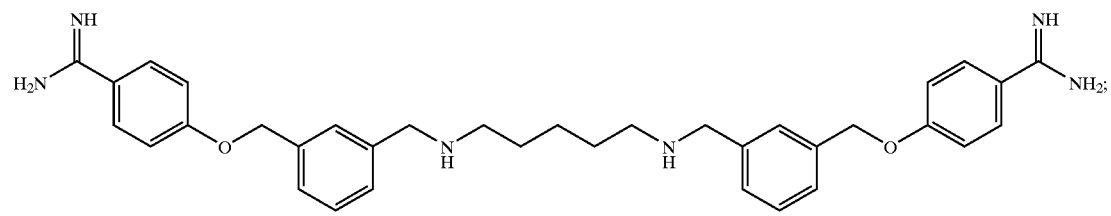
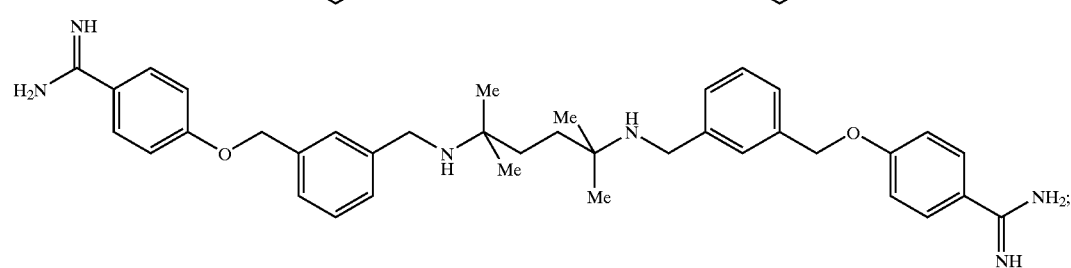

-continued

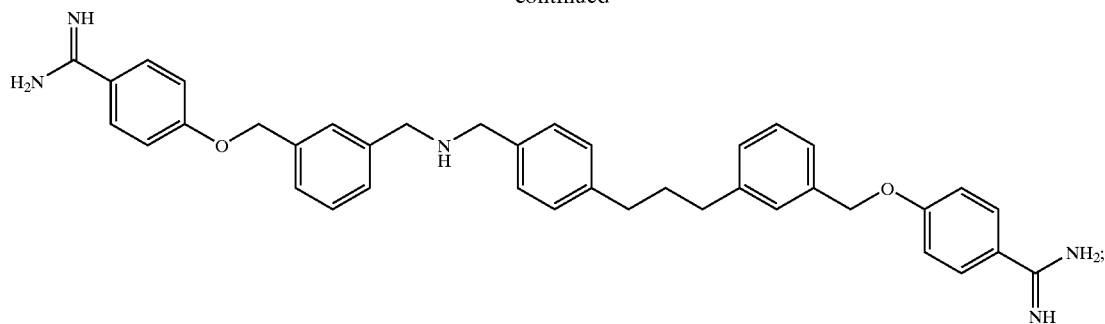

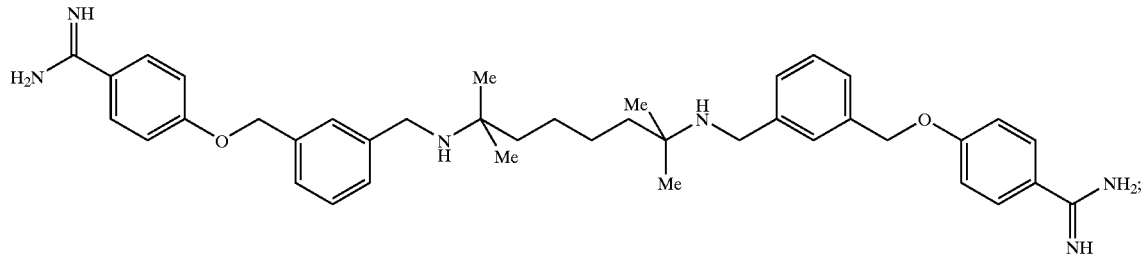

and

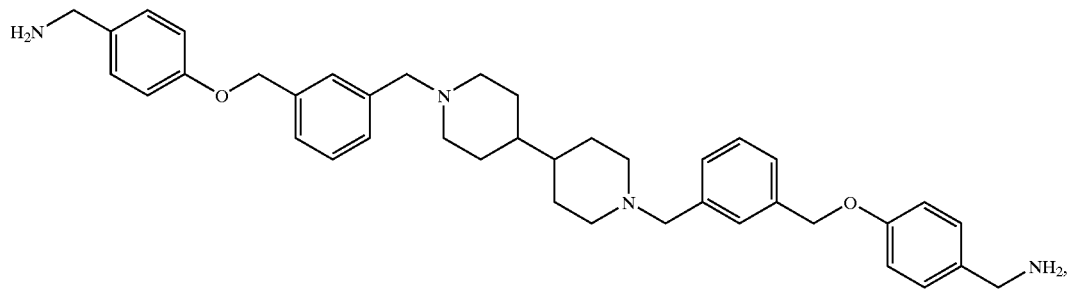

or a pharmaceutically acceptable salt thereof.

23. A method for treating an inflammatory or allergic disease condition which comprises administering to a host suffering from such condition, a therapeutic amount of the compound of formula (I) according to claim 1, the compound of formula (IA) according to claim 8, or the compound of formula (IA1) according to claim 15.

24. The method of claim 23, wherein the disease condition is selected from the group consisting of: bronchial asthma, allergic rhinitis, allergic conjunctivitis, atopic dermatitis, urticaria, allergic otitis, allergic gastrointestinal disorders, Crohn's disease, ulcerative colitis, anaphylactic shock, septic shock, shock lung (ARDS), and arthritis.

25. The method of claim 23, wherein the disease condition is selected from the group consisting of: fibroses fibrosing alveolitis and scarring, collagenoses, scleroderma, arteriosclerosis, and psoriasis.

26. A pharmaceutical composition comprising:

(a) the compound of formula (I) according to claim 1, the compound of formula (IA) according to claim 8, or the compound of formula (IA1) according to claim 15; and (b) a pharmaceutically acceptable carrier.

* * * * *